United States Patent
Pazos-Pérez et al.

(10) Patent No.: US 10,324,038 B2
(45) Date of Patent: Jun. 18, 2019

(54) METHOD FOR DETECTION OF PRESENCE OR ABSENCE OF ANALYTES IN FLUIDS AND AN OPTICAL DETECTION SYSTEM FOR CARRYING OUT THE METHOD

(71) Applicants: Medcom Advance, S.A, Barcelona (ES); Universitat Rovira i Virgili, Barcelona (ES); Fundació Privada Centre Tecnologic de la Química de Catalunya, Tarragona (ES); Fundació Privada Catalana de Recerca I Estudis Avançats, Barcelona (ES); Medcom Tech, S.A, Madrid (ES)

(72) Inventors: Nicolás Pazos-Pérez, Barcelona (ES); Elena Pazos, Barcelona (ES); Carme Catala, Barcelona (ES); Bernat Mir-Simón, Barcelona (ES); Sara Gomez-De-Pedro, Barcelona (ES); Juan Sagales, Barcelona (ES); Carlos Villanueva, Barcelona (ES); Ramon A. Alvarez-Puebla, Barcelona (ES)

(73) Assignees: Medcom Advance, S.A, Barcelona (ES); Universitat Rovira i Virgili, Barcelona (ES); Fundació Privada Centre Tecnologic de la Química de Catalunya, Tarragona (ES); Fundació Privada Institutio Catalana de Recerca I Estudis Avançats, Barcelona (ES); Medcom Tech, S.A, Madrid (ES)

( * ) Notice: Subject to any disclaimer, the term of this patent is extended or adjusted under 35 U.S.C. 154(b) by 0 days.

(21) Appl. No.: 15/749,125

(22) PCT Filed: Jul. 31, 2015

(86) PCT No.: PCT/EP2015/067717
§ 371 (c)(1),
(2) Date: Jan. 31, 2018

(87) PCT Pub. No.: WO2017/020936
PCT Pub. Date: Feb. 9, 2017

(65) Prior Publication Data
US 2018/0217069 A1    Aug. 2, 2018

(51) Int. Cl.
*G01N 21/65* (2006.01)
*G01N 33/58* (2006.01)
(Continued)

(52) U.S. Cl.
CPC ......... *G01N 21/658* (2013.01); *G01N 33/574* (2013.01); *G01N 33/587* (2013.01); *B82Y 15/00* (2013.01); *G01N 33/57415* (2013.01)

(58) Field of Classification Search
None
See application file for complete search history.

(56) References Cited

FOREIGN PATENT DOCUMENTS

WO   WO2015/011231   *   1/2015

OTHER PUBLICATIONS

Qian et al., Surface-Enhanced Raman Nanoparticle Beacons Based on Bioconjugated Gold Nanocrystals and Long Range Plasmonic Coupling, vol. 130, No. 45, pp. 14934-14935, published online Oct. 21, 2008. (Year: 2008).*

(Continued)

*Primary Examiner* — Rebecca L Martinez

(57) ABSTRACT

A method and a system for detection of presence or absence of analytes in fluids, the method comprising the steps of:
a) contacting a fluid sample and a plurality of nanoparticles, the nanoparticles being functionalized with a selective ligand, the contact of the fluid sample with the nanoparticles being under conditions such that, the nanoparticles aggregate selectively on surface of their (Continued)

target analyte, forming a nanoparticle-analyte complex, the aggregation promoting the concentration of the nanoparticles on the surface of the target analyte;

b) subjecting a fluid mixture of the fluid sample and the plurality of nanoparticles to SERS;

c) measuring at least a SERS signal associated with the fluid mixture;

d) spectrally analyzing the at least one SERS signal of step c);

e) recognizing at least one defined SERS spectrum of the nanoparticle-analyte complex, through a SERS signal enhanced by the at least one narrow inter-nanoparticle gap.

7 Claims, 16 Drawing Sheets

(51) Int. Cl.
*G01N 33/574* (2006.01)
*B82Y 15/00* (2011.01)

(56) References Cited

OTHER PUBLICATIONS

International Search Report and the Written Opinion dated Apr. 25, 2016 From the International Searching Authority Re. Application No. PCT/EP2015/067717. (15 Pages).

Graham et al. "Control of Enhanced Raman Scattering Using A DNA-Based Assembly Process of Dye-Coded Nanoparticles", Nature Nanotechnology, XP055264551, 3(9): 548-551, Published Online Jul. 11, 2008. Abstract, Fig.1c, p. 548, r-h col., Last Para—p. 549, l-h col.

Lee et al. "DNA-Gold Nanoparticle Reversible Networks Grown on Cell Surface Marker Sites: Application in Diagnostics", ACS Nano, XP055264585, 5(3): 2109-2117, Published Online Feb. 11, 2011. Abstract, Figs.2, 3, p. 2110, p. 2111, l-h col., Last Para, p. 2113, l-h col.

Qian et al. "Surface-Enhanced Raman Nanoparticle Beacons Based on Bioconjugated Gold Nanocrystals and Long Range Plasmonic Coupling", Journal of the American Chemical Society, JACS, XP055264942, 130(45): 14934-14935, Nov. 12, 2008. p. 1434, l-h col., Para 3—p. 1435, l-h col., Figs. 1-3.

\* cited by examiner

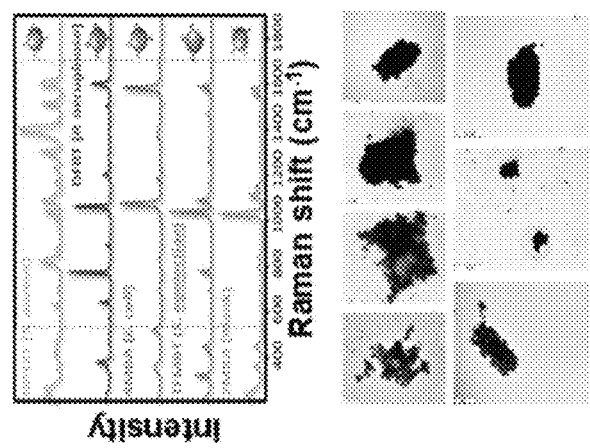
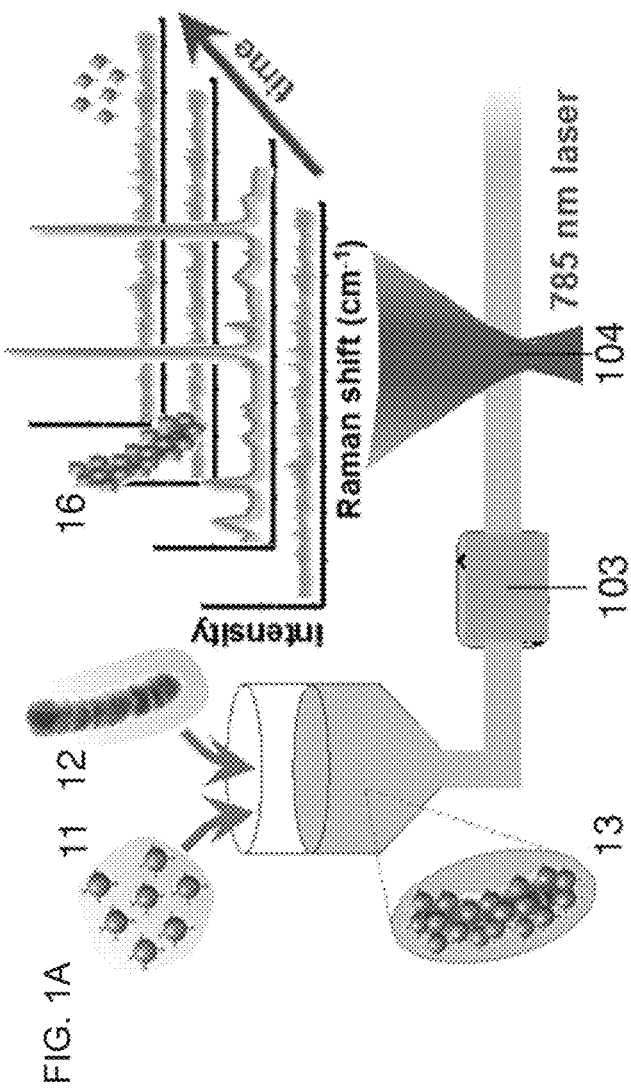
FIG. 1A
FIG. 1B
FIG. 1C

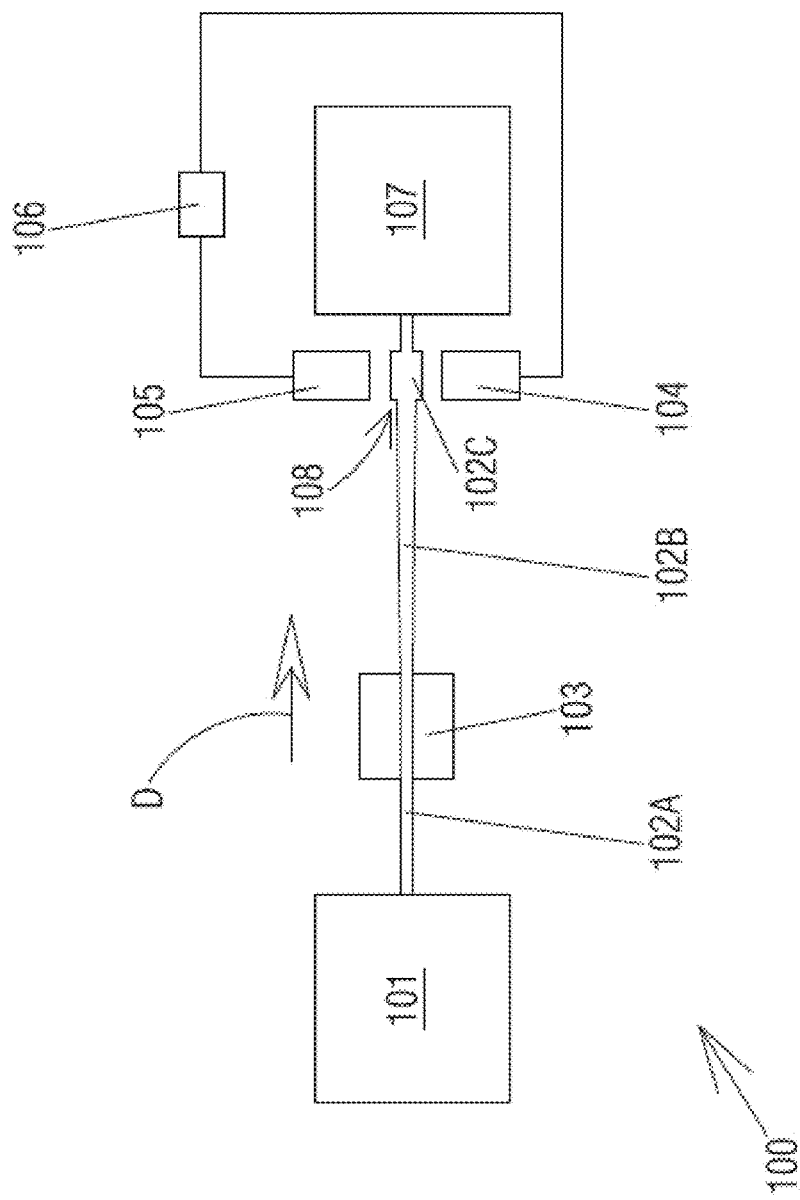

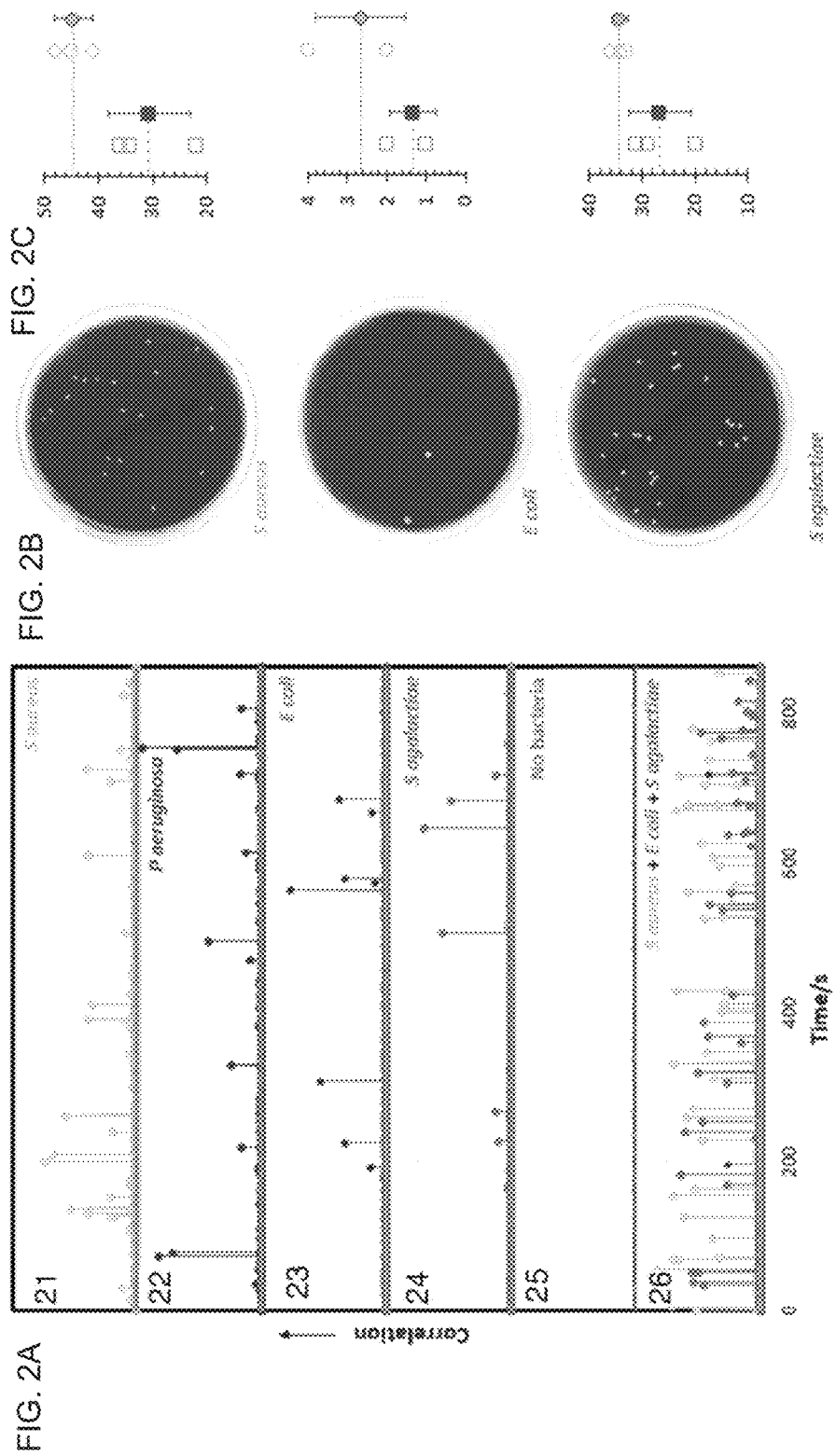

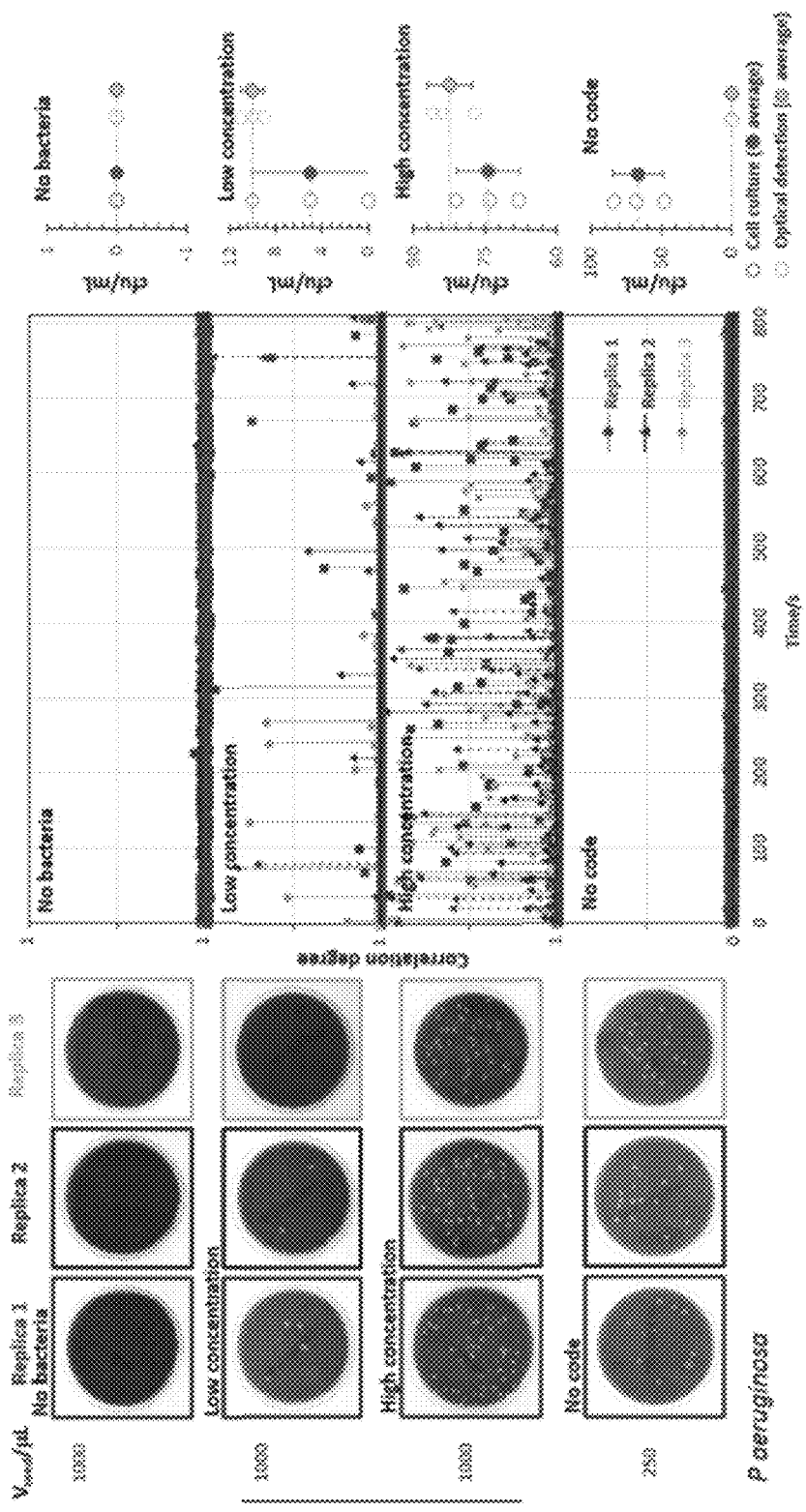

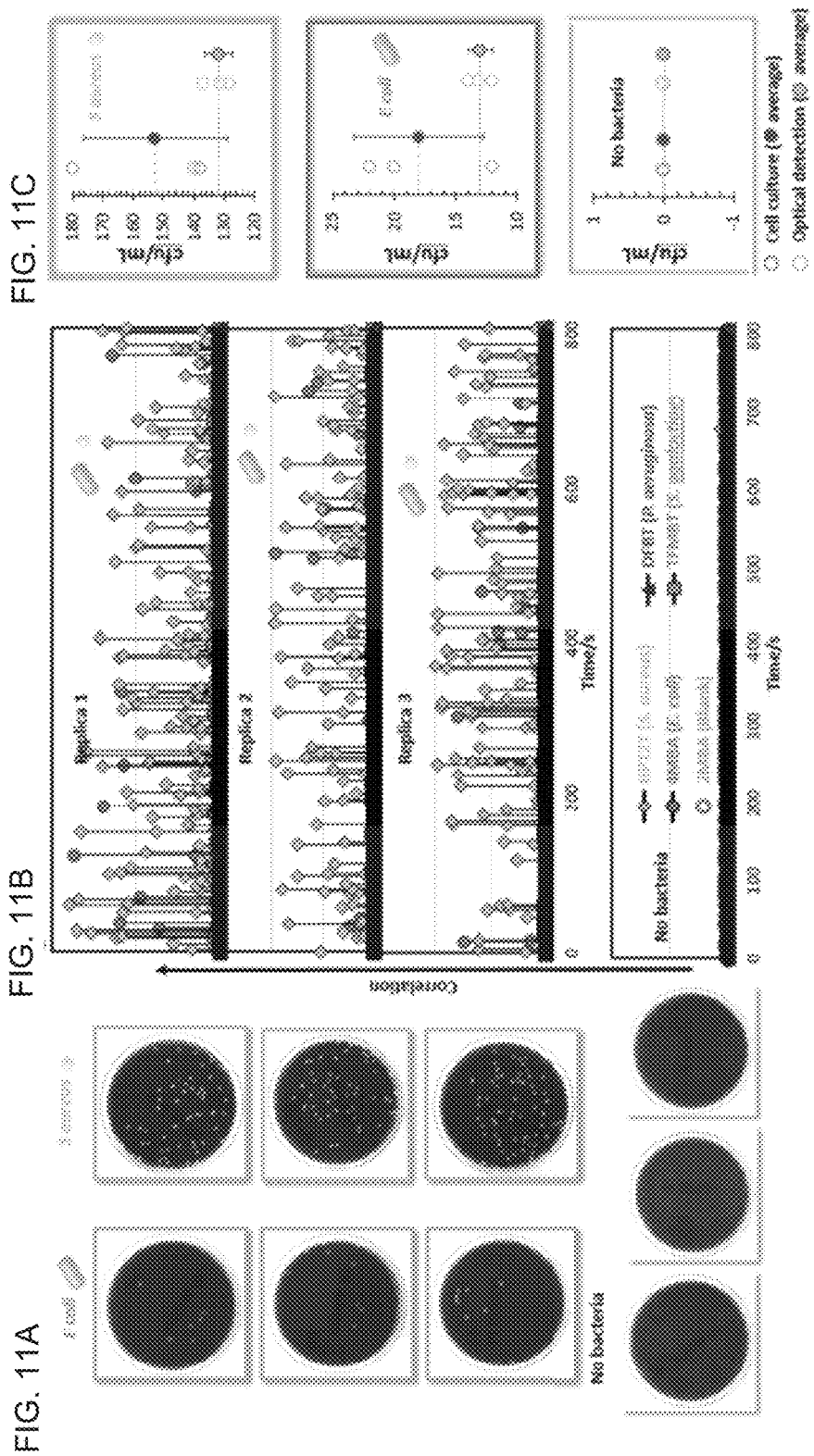

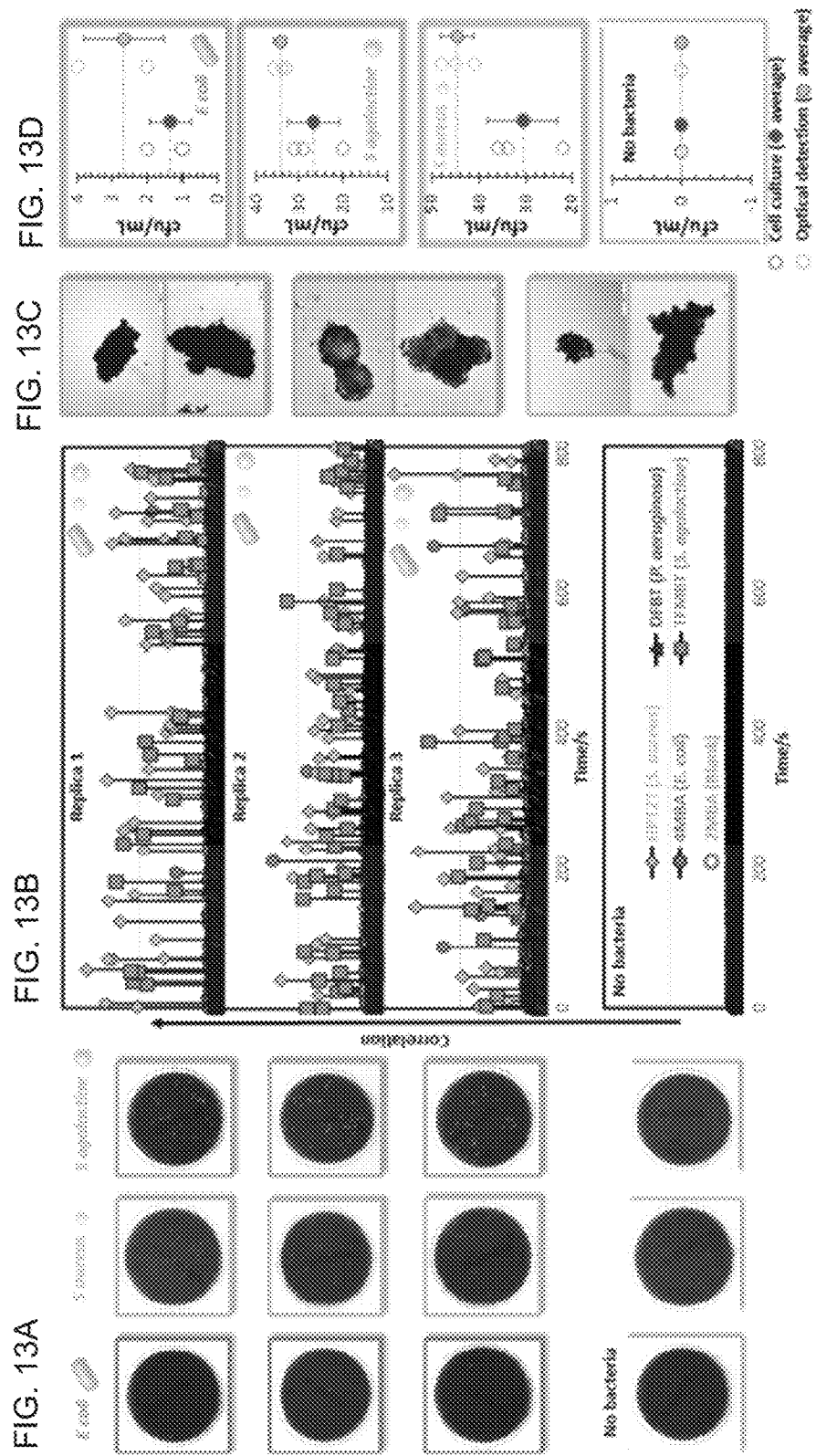

METHOD FOR DETECTION OF PRESENCE OR ABSENCE OF ANALYTES IN FLUIDS AND AN OPTICAL DETECTION SYSTEM FOR CARRYING OUT THE METHOD

OBJECT OF THE INVENTION

The present invention is related to a method for detection of presence or absence of analytes in fluids and an optical detection system for carrying out such method by using the surface-enhanced Raman scattering (SERS) that incorporates considerable innovations and advantages.

More specifically, the invention refers to a method based on the use of SERS-scattering technology applied to direct real-time multiplexed plasmonic identification and quantification of analytes in fluid samples through hotspots generated by inter-nanoparticle gaps. The invention also refers to a system for carrying out the method.

The object of the invention also provides a relatively fast, easy and comfortable way for detecting and quantifying any kind of analyte in samples of fluids.

BACKGROUND TO THE INVENTION

Sepsis affects nearly 20 million people per year with a mortality rate of 30-40%[1]. These patients require intensive care with associated high costs, which impose significant health-care, economic, and social burdens. In particular, each septic patient in the United States incurs costs of approximately $25,000 during hospitalization, totaling a nationwide annual bill in excess of $17 bn[1]. The time to initiation of effective antimicrobial therapy is known to be the single strongest predictor of outcome, as every hour delay in its administration increases by 8% the risk of death[2]. Besides the obvious economic benefits, the development of fast, accurate, and inexpensive diagnostic methods thus appears as a major goal for alleviating human pain. Microbial culture remains the most widespread technique for identifying the infectious agent, but unfortunately it requires 24-72 hours to provide a conclusive diagnosis for common infections. Understandably, a large deal of work has been devoted over the last three decades to developing alternative methods for fast identification of bacteria in suspected patients[3]. These methods include immunology-based approaches (e.g., enzyme-linked immunosorbent assay (ELISA), as well as fluorescence and radio immunoassays)[4], nucleic acid identification (e.g., polymerase chain reaction (PCR))[5], and spectrometry-based procedures (e.g., matrix-assisted laser desorption/ionization-time-of-flight (MALDI-TOF) mass spectrometry)[6]. Although generally faster than just sequential microbial culture, these techniques still require hours to days, depending on the pathogen. Additionally, immunological and nucleic acid tests are expensive (around $200 each) and monoplex (one test per target microorganism), while MALDI-TOF still relies on microbial culture to isolate pure colonies. As a consequence, a broad-spectrum antibiotic is generally recommended to cover all potential pathogens until obtaining a conclusive identification. Apart from its inherent cost and adverse health effects, this indiscriminate use of antibiotics induces bacterial resistance, a growing problem of modern pharmacopeia[7]. Society therefore urges for the development of new diagnostic systems capable of providing fast, accurate, inexpensive, and if possible multiplexed identification of infectious agents in body fluids[8].

The same problems arise with any kind of analyte instead of microorganisms, since rapid and easy identification and quantification of analytes on fluids, for instance a sample of blood, is of the outmost importance.

Recent advances in nanoscience, spectroscopy, magnetism, plasmonics, and microfluidics have generated great expectations for the development of new approaches to bacteria detection[9-12]. Unfortunately, the methods so far proposed are generally time consuming, capable of only exploring small sample volumes (~microliters), working exclusively for one a priori selected pathogen[9], not truly multiplex[10], requiring from external labels[11], or relying on additional steps to record a suitable signal for identification[12].

Therefore, there is still a need for improved methods and systems for identification and quantification of analytes in fluids reducing the complexity, length of time and allowing working with a relatively large volume sample.

DESCRIPTION OF THE INVENTION

The present invention has been developed for the purpose of providing a method for detection of presence or absence of analytes in fluids and an optical detection system for carrying out such method that solves the above-mentioned disadvantages, in addition contributing other additional advantages that will become clear from the description that is given below.

In the present document, the term "analyte" shall be understood as any biological entity to be detected and in the broadest sense this term refers to any substance with the capacity to bind to a ligand of the encoded and/or biofunctionalized nanoparticles. By way of non-limiting illustration, the term "analyte" includes eukaryotic and prokaryotic cells, including circulating tumoral cells, pathogenic and no pathogenic microorganism (i.e. fungi, protozoa, algae, rotifers, bacteria and archaea), viruses, nucleic acids, peptide nucleic acids, antigens, peptides and proteins, or the combination thereof.

In the sense used in this document, the term "microorganism" includes very small or microscopic organisms which can be single unicellular, clustered unicellular (i.e. colony forming units, CFU) or multicellular organisms. The concept of "microorganism" lacks any taxonomic or phylogenetic implication since it encompasses unicellular organisms not related to one another.

The term "fluid" will be understood in the present specification as any kind of substance that is capable of flowing, as a liquid or a gas.

It is therefore, an object of the invention to provide a method for detection of presence or absence of analytes in fluids comprising the steps of:

a) contacting a fluid sample and a plurality of nanoparticles, wherein each of the nanoparticles comprises a core unprotected and tagged with at least a molecular species with a defined SERS spectrum, the nanoparticles being functionalized with at least a selective ligand for a given receptor of a target analyte, the contact of the fluid sample with the nanoparticles being under conditions such that, when the fluid sample comprises at least an analyte the nanoparticles aggregate selectively on surface of their target analyte, forming a nanoparticle-analyte complex, the aggregation promoting the concentration of the nanoparticles on the surface of the target analyte and thus a plasmon coupling in between the nanoparticles through the generation of narrow inter-nanoparticle gaps;

b) subjecting a fluid mixture of the fluid sample and the plurality of nanoparticles to SERS;

c) measuring at least a SERS signal associated with the fluid mixture;

d) spectrally analysing the at least one SERS signal of step c);

e) recognizing at least one defined SERS spectrum of the nanoparticle-analyte complex, through a SERS signal enhanced by the at least one narrow inter-nanoparticle gap, when the fluid mixture comprises at least a nanoparticle-analyte complex with the narrow inter-nanoparticle gap.

It should be noted that the method object of the present invention is not practised on the human or animal body and any fluid sample taken from the body is not returned to the living body.

Due to these characteristics, a method for detection of the presence or absence of analytes in fluids is achieved that provides for fast exhaustive analyte identification by screening large fluid sample volumes (e.g., milliliters of fluid) for analyte content. The application on the medical field can provide the identification and quantification of microorganisms by screening milliliters of blood for microorganism content, as required by standard medical practice for the analysis of biological samples[13]. Label-free detection and quantification of analyte in real time and in a multiplexed manner are achieved.

The use of nanoparticles tagged with Raman codes, functionalized and unprotected promotes the generation of optical hotspots when these nanoparticles aggregate on the analyte and form narrow inter-nanoparticle gaps. The presence of one of the target analytes triggers an accumulation of its partner nanoparticles at the surface of the analyte, rapidly reaching full random coverage[14]. Multiple narrow gaps between nanoparticles are then produced, which act as hotspots in which Raman scattering is enhanced by several orders of magnitude relative to non-interacting nanoparticles.

Additionally, the accumulation of nanoparticles on the analyte produces an increased SERS signal relative to the less abundant nanoparticles in the rest of the fluid. The mechanism for identification is thus double: first by accumulation of nanoparticles on the analyte, which results in an increased SERS signal, and second because of the formation of narrow inter-particle gaps. The former produces a relatively moderate increase in SERS signal, whereas the latter results in orders of magnitude increase, and thus strongly facilitates the detection of the analyte through this increase in SERS signal.

The fluid sample to be analysed may contain none, one or more different analytes (for which the nanoparticles have been selectively functionalized with the appropriate selective ligand or ligands, with at least one selective ligand for each type of the targeted analytes). It should be noted that the nanoparticles are not functionalized farther to promote plasmonic coupling upon aggregation on the analyte surface.

The selective ligand may be an antibody, protein, aptamer (i.e. macromolecules) or a small molecule.

The expression "unprotected nanoparticle" has to be understood in the present specification to a nanoparticle which comprises a core made of a material capable of generating high electric or electromagnetic fields at the particle surface by means of the interaction thereof with a light beam. The core is void of any kind of coating, as for instance a coating comprising silicon dioxide ($SiO_2$) or polymer, that may prevent plasmonic couplings between a pair of nanoparticles or among several nanoparticles and/or increases the nanoparticle colloidal stability.

The expression "narrow" internanoparticle gap has to be understood in the present specification to a gap in between two nanoparticles for nanoparticles, such gap having a length between two nanoparticles lower of a few nanometers (e.g., 1 nm, or 2 nm, or lower than 30 nm).

Unlike the prior art, an array of unprotected nanoparticles on the analyte is promoted in order to achieve the interaction of optical electrical fields induced by the nanoparticles on each other when being struck by the light beam.

In a preferred form, the method further comprises circulating the fluid mixture of the fluid sample and the plurality of nanoparticles through at least a passage and an incident monochromatic light is allowed to strike the fluid mixture of the fluid sample and the plurality of nanoparticles in step b). The incident monochromatic light is allowed to strike the fluid mixture passing through a detection section associated with the passage.

The method may comprise an advantaging step after the above described step e) which is the step f) quantifying the number of recognized defined SERS spectra (positive event) and the intensity of the SERS signal related to each recognized defined SERS spectra in the fluid mixture. Unlike the prior art methods, the present method can quantify the analyte on a relatively large fluid sample volume in a real-time way. For providing real time quantification and identification, in step d) of the present method for detection of presence or absence of analytes in fluids a spectrum is recorded in predefined lapses of time.

The above mentioned selective ligand may be advantageously any cancer cell marker. For instance, but not exclusively:

1—MUC1 . . . ab28081
2—CK 8, 18 y 19 . . . ab41825
3—EpCAM . . . ab28081
4—CEA . . . ab4451
5—HER-2 . . . ab16901 (only breast and gastric)
6—N-CADHERIN . . . ab6528
7—CD146 . . . ab75769

Another object of the invention is an optical detection system for carrying out the method of detection of presence or absence of analytes in fluids according to any of the preceding claims, which comprises:

a mixing container configured to receive and mix a fluid sample and a plurality of unprotected nanoparticles;

at least a passage in fluid communication with the mixing container;

driving means associated with the passage;

an emitter adapted to produce an incident monochromatic light to strike on a fluid mixture of fluid sample and a plurality of nanoparticles in a detection section associated with the passage;

a reader configured to receive a reflected, transmitted, or scattered light from the fluid mixture of the passage and reading the Raman signal associated with the fluid mixture;

control means in data communication with the emitter and the reader.

These features allow obtaining a system for implementing the method object of the present invention. The results of detection are the presence or absence of analytes and also the quantification of the present analytes, which are rapidly obtained, without any culture like the prior art. Unlike the prior art, the reader can receive the enhanced Raman signal associated with the inter-nanoparticle gap which acts as a hotspot. A relatively large amount of fluid sample can be screened, for instance milliliters of blood.

The passage used in the present system may be preferably a microchannel with variable dimensions.

According to another feature of the system, the driving means may be of a passive type or an active type. When the driving means is of the passive type it comprises the passage configured to allow capillary motion and when the driving means is of the active type it comprises a pump, particularly a micropump.

The incident monochromatic light produced by the emitter is a laser beam from the UV to the infrared. The wavelength of monochromatic light may be preferably of 785 nm.

Other characteristics and advantages of the method for detection of presence or absence of analytes in fluids and the optical detection system for carrying out such method objects of this invention will become clear from the description of preferred, but not exclusive, embodiments, the drawings that are attached are by way of illustration but without being in any way limiting.

BRIEF DESCRIPTION OF THE DRAWINGS

FIG. 1A schematically shows a diagram of operation of an optical detection system with some relevant parts according to the invention;

FIG. 1B shows SERS spectra of the different coded particles used for targeted analytes (bacteria);

FIG. 1C shows images of a transmission electron microscope of targeted analytes (bacteria) covered with their respective matching nanoparticles;

FIG. 1D is a diagrammatical view of an optical detection system according to the invention;

FIG. 2A shows a temporal series of correlations between sequentially acquired spectra collected over 270 ms intervals and the SERS reference of the labeled nanoparticles;

FIG. 2B shows images of cellular cultures (24-48 hours) for microorganisms inoculated in blood samples;

FIG. 2C shows comparisons of bacteria concentrations as determined by the present invention (open circles) for a contaminated sample versus traditional cultures (open squares);

FIG. 10A shows images of cellular cultures for an analyte (*P. aeruginosa* bacteria); a serum sample is spiked with *P. aeruginosa* at different concentrations;

FIG. 10B shows the detection and quantification results obtained in the present system: with no bacteria present, at low concentration, high concentration and high concentration but without the encoded nanoparticle that identifies the analyte (*P. aeruginosa* bacteria);

FIG. 10C shows a statistical comparison of methods of FIGS. 10A and 10B:

FIG. 11A shows images of cellular culture of serum sample spiked with *E. coli* and *S. aureus* (volume seeded 1 mL for *E. coli* and 0.5 mL for *S. aureus*);

FIG. 11B shows detection and quantification results obtained in the present system for the same bacteria as FIG. 11A;

FIG. 11C shows statistical comparison of methods of FIGS. 11A and 11B;

FIG. 13A shows images of cellular culture of serum sample spiked with *E. coli*, *S. agalactiae* and *S. aureus* (Volume 0.5 mL for each);

FIG. 13B shows detection and quantification results obtained in the present system for the same bacteria as FIG. 13A;

FIG. 13C shows representative TEM images of coated bacteria;

FIG. 13D shows statistical comparison of methods of FIGS. 13A and 13B:

DESCRIPTION OF A PREFERRED EMBODIMENT

Figures 3A, 3B, 3C, 3D:
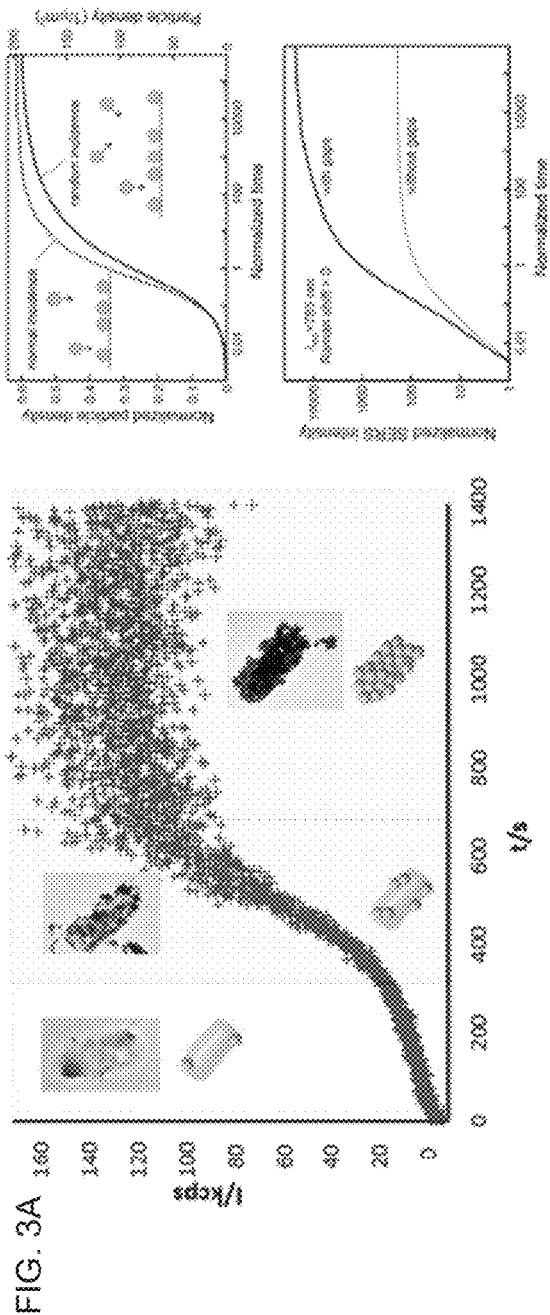
FIG. 3A shows the kinetics of nanoparticle aggregation as measured through the time-dependent SERS signal (symbols) after adding analyte (*E. coli*) to the mixture of coded nanoparticles.
FIG. 3B shows a Monte Carlo simulation of the temporal evolution of nanoparticle aggregation on the analyte (bacteria membrane) produced by random encounters.
FIG. 3C shows an estimated increase in SERS intensity with (solid curve) and without (broken curve) inclusion of the effect of inter-nanoparticle gap hotspots, as extracted from the simulation of FIG. 3B.
FIG. 3D shows a scheme of an analyte (*E. coli*) individual covered with coded nanoparticles, and a detail of the near-electric-field intensity distribution revealing the formation of optical hotspots at the nanoparticle gaps in a representative distribution of nanoparticles.

The attached figures show preferred and non-limiting embodiments of an optical detection system designated in a general way with reference number 100 and different views regarding the method for detection of presence or absence of analytes, objects of the present invention.

A preferred embodiment of an optical detection system 100 for detection of presence or absence of analytes in fluids according to the invention can be seen in FIG. 1D, wherein it is shown that the optical detection system 100 comprises a mixing container 101 or inlet vessel configured to receive and mix a fluid sample with or without at least a target analyte and a plurality of unprotected nanoparticles. The fluid sample may encompass at least one target analyte (FIG. 1A) and the nanoparticle can encompass a plurality of encoded and unprotected nanoparticles (FIG. 1A). The mixing container 101 may comprise the precharged nanoparticles and the fluid sample may be placed later to obtain the corresponding mixture. The nanoparticles may be provided as a "cocktail" containing several types thereof, for instance from 1 to 200, each type selectively targeting a different analyte.

The optical detection system 100 also comprises a passage 102A, 102B, 102C in fluid communication with the mixing container 101. This passage 102A, 102B, 102C is a microchannel with variable dimensions, for instances it has a width of 200 µm and a depth of 100 µm, which is enlarged to 400 µm-width and 2 mm-depth in a detection section 108.

For circulating the fluid mixture of nanoparticles and fluid sample following the direction D indicated by an arrow in FIG. 1D, the system comprises driving means associated with the passage 102A, 102B, 102C. The driving means comprises preferably a pump 103, particularly a micropump (mp6, Bartels). However, the passage 102A, 102B, 102C may be configured to allow capillary motion of the fluid mixture.

The passage 102A, 102B, 102C is preferably divided in three sections; a narrow initial section of the passage 102A that increases pressure drop of the flow necessary to finely control flow discharge with the micropump. Next, a second section of the passage 102B expands the volume of the microchannel until the third section of the passage 102C where dimensions of the microchannel increase until 0.4 mm width and 2 mm depth. This final volume gives the appropriate dimensions to continuously screen the fluid mixture with flow rates for instance of 1.74 mm s$^{-1}$ at a capture rate of 1.83 mm s$^{-1}$ The system also comprises an emitter 104 adapted to produce an incident monochromatic light L to strike on the mixture flowing through the passage 102A, 102B, 102C. It should be understood that any means capable of producing such light may be used, for instance a device comprising a macroobjective 6 mm D and −18 mm focal, providing an efficient spot of 0.5 mm, with the laser emitting at 785 nm and 300 mW.

Following with the system, it also comprises a reader 105 configured to receive a reflected transmitted, or scattered light (not shown) from the mixture of the passage 102A, 102B, 102C, particularly the mixture passing through the detection section 108, and reading the enhanced Raman signal associated with the fluid mixture of nanoparticles and the fluid sample or more particularly, the Raman signal of the nanoparticle-analyte complex and the enhanced Raman signal by the inter-nanoparticle gap when at least one analyte is comprised in the fluid sample. As per the emitter 104, the reader 105 has to be understood as any device capable of receiving the reflected light from the mixture of the passage 102A, 102B, 102C, specifically from the inter-nanoparticle gaps. The emitter may comprise for instance a spectrometer Renishaw Invia Reflex device.

Control means 106, as a processor, in data communication with the emitter 104 and the reader 105 is comprised by the present system and can also control the micropump operation.

A particularly preferred embodiment of the present system may comprise a layer (not shown) with a slide cover (not shown) by way of a microfluidic device. The layer is fabricated with polydimethylsiloxane (PDMS) by replica molding using an aluminum master mold. PDMS (Sylgard 184, Dow Corning) is prepared by mixing pre-polymer and curing agent at a standard 10:1 ratio. The mixture is poured onto the mold, degassed in vacuum, and cured at 80° C. After an hour, PDMS is peeled off the mold and fluidic access holes (inlet and outlet, not illustrated) are punched.

The microfluidic device is obtained by bonding the PDMS layer to a slide cover (130-170 µm-thick) after oxygen plasma treatment (100 W, 3% O2, 0.2 mbar, 40 s) (Plasma Flecto 10, Plasma technology GmbH). The microfluidic device comprises a microchannel formed during a moulding step of the layer and the matching slide cover.

The mixing container 101, the pump 103, and an outlet vessel 107 associated with the mixing container 101 through the passage 102A, 102B, 102C for receiving the mixture after the screening, are installed on the microfluidic device. Then microfluidic device is connected to the emitter 104 and the reader 105 for carrying out the method of the present invention.

However, it is obvious that the system may adopt any embodiment other than the microfluidic device.

For detecting the presence or absence of target analytes in a fluid sample, the present invention also discloses a method which comprises the steps of:

a) contacting a fluid sample and a plurality of nanoparticles, wherein each of the nanoparticles comprises a core unprotected and tagged with at least a molecular species with a defined SERS spectrum, the nanoparticles being functionalized with at least a selective ligand for a given receptor of a target analyte, the contact of the fluid sample with the nanoparticles being under conditions such that, when the fluid sample comprises at least an analyte the nanoparticles aggregate selectively on surface of their target analyte, forming a nanoparticle-analyte complex, the aggregation promoting the concentration of the nanoparticles on the surface of the target analyte and thus a plasmon coupling in between the nanoparticles through the generation of narrow inter-nanoparticle gaps;

The nanoparticles can be obtained by labelling silver nanoparticles with different Raman-active molecules and functionalizing them for instance with ligands as bacteria-selective antibodies or cancer cell markers (see reference 11 in FIG. 1A). Fluid nanoparticle dispersion is mixed in the mixing container 101 with the sample fluid, which might contain microorganisms as target analytes (see reference 12 in FIG. 1A). Several types of bacteria may be targeted using nanoparticles prepared with different specific combinations of Raman molecules and ligands (for instance antibodies). The presence of one of the targeted analyte (e.g. microbes) induces aggregation of its antibody-matching nanoparticles on its surface, rapidly evolving towards full random coverage (see reference 13 in FIG. 1A).

The fluid mixture is circulated through the passage 102A, 102B, 102C driven by the pump 103 following direction D;

b) subjecting a fluid mixture of the fluid sample and the plurality of nanoparticles to SERS. The fluid mixture of fluid sample and nanoparticles is passed through the detection section 108 where the emitter 104 issues an incident monochromatic light (laser beam) with a wavelength for instance of 785 nm to strike the mixture. The wavelength may vary from UV to infrared;

c) measuring at least a SERS signal associated with the fluid mixture. All the portions of the fluid mixture are subjected to SERS and the signal produced is measured (intensity) by the system. If the fluid mixture comprises an analyte-nanoparticle complex with the narrow inter-nanoparticle gap, the intensity measured would be increased exponentially in between 2 to 3 order of magnitude per gap. The majority of the time steps the present system only sample dispersed nanoparticles, which produce a weak Raman signal. Occasionally, target analytes (e.g. microorganisms) traverse the light beam issued by the emitter 104, giving rise to several orders of magnitude higher Raman signal[15] because the analyte surface is coated with a dense array of narrow inter-particle gaps that act as optical hotspots, thus exposing the Raman molecules to a much higher light intensity and yielding an intense signal that reveals the molecular fingerprints, and consequently, also the type of the analyte (e.g. specific cells, microorganisms, viruses, nucleic acids, peptide nucleic acids, antigens, peptides and proteins or a combination thereof) (see FIG. 1B);

d) spectrally analysing the at least one SERS signal of step c). If the fluid mixture comprises an analyte-nanoparticle complex with the narrow inter-nanoparticle gap, the enhanced Raman signal associated with the narrow inter-nanoparticle gap is analysed to record the inelastic signal generated by the Raman-active molecules (see reference 16 in FIG. 1A). A spectrum may be acquired and recorded in predefined lapse of time, for instance about every 1-30 ms.

e) recognizing at least one defined SERS spectrum of the nanoparticle-analyte complex, through a SERS signal enhanced by the at least one narrow inter-nanoparticle gap, when the fluid mixture comprises at least a nanoparticle-analyte complex with the narrow inter-nanoparticle gap.

After step e) the present method may comprise the step f), for quantifying the analyte in the fluid sample, when an analyte is comprised in the fluid sample. For instance milliliters of sample fluid can be exhaustively scrutinized following this method, quantifying the amount of target analytes in the fluid sample.

That quantification is achieved by quantifying the number of recognized defined SERS spectra (positive events) and the intensity of the SERS signal related to each recognized defined SERS spectra (positive event) in the fluid mixture.

It is obvious that if no analyte is comprised in the fluid sample, the system would not obtain an enhanced SERS signal of both the nanoparticle-analyte complexes and the narrow inter-particle gaps. Therefore, the absence of the analyte in the fluid sample would be detected.

The above describe method may follow a sequence of instructions of a computer program implemented with the control means 106 or alternatively with a computer (not shown) in data communication with the present system. To this end, control means 106 may store the source code in order to automate the method or may be stored in any computer-readable medium in data communication with the system for executing the computer program. The sequence of instructions may be obviously adapted to particular conditions of analysis.

Regarding the above described method, several tests were made by the inventors with the aim to demonstrate selectivity and multiplexing of the present system in real analyte samples. Although tests are related to bacteria detection, the analytes to be detected may vary as above mentioned. The present method and system are not limited to detection of bacteria. Such tests are described in the following with reference to the attached figures.

Before continuing with the tests, the previous experimental values, method and conditions used and followed should be cited.

Materials and Methods:

Silver nitrate (99.99%, AgNO3), trisodium citrate dihydrate (≥99.5%), L-ascorbic acid (≥99.0%), magnesium sulfate (≥99.0%, MgSO4), ethanol (99.5%, EtOH), 11-mercaptoundecanoic acid (95%, MUA), 4-mercaptobenzoic acid (99%, MBA) thiosalicylic acid (97%, TSA), 3,4-difluorothiophenol (96%, DFTP), 2-(trifluoromethyl)benzenethiol (96%, TFMBT), 1-(4-hydroxyphenyl)-1H-tetrazole-5-thiol (97%, HPHTT), bovine serum albumin (≥98.0%, BSA), N-(3-dimethylaminopropyl)-N'-ethylcarbodiimide hydrochloride (BioXtra, EDC), sodium chloride (BioXtra, ≥99.5%, NaCl), Dulbecco's phosphate buffered saline (D8537, DPBS) and human blood (BCR634 FLUKA) were purchased from Sigma-Aldrich. All reactants were used without further purification. Milli Q water (18 MΩ cm$^{-1}$) was used in all aqueous solutions, and all the glassware and magnetic stirrers were cleaned with aqua regia and with a potassium hydroxide solution in isopropanol/water before all the experiments.

*Escherichia coli* (ab30522, *E. coli*) and *Streptococcus agalactiae* (ab41203, *S. agalactiae*) antibodies (Ab) were purchased from Abcam, and *Pseudomonas aeruginosa* (MA1-83430, *P. aeruginosa*) and *Staphylococcus aureus* (MA1-83467, *S. aureus*) antibodies were purchased from life technologies. Enriched thioglycollate medium (221742, BBL) was purchased from BD (Becton, Dickinson and Company) and Columbia agar+5% sheep blood plates (43 041) were purchased from bioMérieux. Bacterial samples were obtained from Department of Clinical Microbiology, Hospital Clinic, School of Medicine, University of Barcelona, Barcelona, Spain.

Synthesis of Citrate-Stabilized Spherical Silver Nanoparticles:

Spherical silver nanoparticles (Ag nanoparticles) of approx. 62 nm in diameter were produced by a combination of previously reported approaches[16-19]. Briefly, 250 mL of Milli Q water were heated under vigorous stirring. A condenser was used to prevent solvent evaporation. Next, aqueous solutions of trisodium citrate (3.41 mL, 0.1 M) and ascorbic acid (0.25 mL, 0.1 M) were consecutively added into the boiling water. After 1 minute, a premixed aqueous solution containing AgNO$_3$ (0.744 mL, 0.1 M) and MgSO$_4$ (0.56 mL 0.1 M), which was previously incubated at room temperature for 5 min, was rapidly injected into a reaction vessel under vigorous stirring. The color of the solution quickly changes from colorless to yellow and gradually changes into dark orange. Boiling was continued for 1 h under stirring to ensure the completeness of the reaction.

The size of the Ag nanoparticles was approximately 62 nm. The silver concentration of the synthesized particles was $2.5 \times 10^{-4}$ M.

Mercaptoundecanoic Acid Functionalization and Codification of Ag Nanoparticles:

Next, MUA was used in order to provide colloidal stability to the Ag nanoparticles during the encoding process and later on to use the carboxylic functionality for the coupling of the antibodies. Specifically, five aliquots (25 mL each) of the synthesized Ag nanoparticles were cleaned by centrifugation (5400 rpm, 30 min) and redispersed via sonication (during 5 min) in a solution containing Milli Q water (3.27 mL) and EtOH (21.67 mL). Consequently, the Ag nanoparticles were functionalized with a small amount of MUA (2.4 molecules $nm^{-2}$) by adding rapidly a solution containing MUA (24.76 µL, $1.0 \times 10^{-3}$ M in EtOH) and $NH_4OH$ (30 µL, 29% aqueous solution) to each aliquot under vigorous stirring. Agitation was continued for 28 h to assure the complete MUA functionalization on the silver surface. Finally, the MUA functionalized Ag nanoparticles aliquots were then encoded with five different Raman labels (1.6 molecules $nm^{-2}$ of MBA, TSA, DFTP, TFMBT, and HPHTT, respectively). To this end, 16.51 µL of a $10^{-3}$ M stock solution of the five different SERS codes were added to the aliquots under strong magnetic stirring. Once more, stirring was continued for another 28 h. The encoded Ag nanoparticles solutions were then centrifuged and redispersed twice in Milli Q water to remove the $NH_4OH$, the EtOH, and any unreacted Raman label prior antibody coupling. Nanoparticles concentration was calculated for each aliquot using the Lambert-Beer's law and an extinction coefficient of $7.79 \times 10^{10}$ $M^{-1}$ $cm^{-1}$, derived from literature,[20] and adjusted to 0.14 nM for all of them. On the other hand, another aliquot (25 mL) of the synthesized Ag nanoparticles was cleaned also by centrifugation (5400 rpm, 30 min) and redispersed in Milli Q water (25 mL). The Ag nanoparticles were then functionalized with MUA by adding, under vigorous stirring, 24.76 µL ($1.0 \times 10^{-3}$ M in EtOH). Agitation was continued for 28 h to assure the complete MUA functionalization on the silver surface. Finally, Ag nanoparticles were further modified with BSA (41.26 µL, $1.0 \times 10^{-3}$ M in Milli Q water) under magnetic stirring for 24 h, followed by one cleaning step centrifugation to remove excess of BSA and any unreacted MUA molecules (5400 rpm, 30 min, redispersed in Milli Q water). Nanoparticles concentration was calculated and adjusted to 0.034 nM.

Antibody Conjugation to Ag Nanoparticles:

200 µL of DPBS and EDC (39.2 µL, 250 nM in DPBS) were added over each codified Ag nanoparticles solution (1 mL, 0.14 nM, Raman labels: MBA, TSA, DFTP, TFMBT, and HPHTT), the mixtures were shaken for 5 min at room temperature, and then the antibodies solutions were added (1.46 µL, ~6.67 µM, *E. coli*, BSA, *P. aeruginosa, S. agalactiae*, and *S. aureus*, respectively). The resulting mixtures were shaken for 2 h at room temperature, then were cleaned twice by centrifugation to remove the excess of unreacted EDC and antibodies (3000 rpm, 10 min), and redispersed in DPBS/Milli Q water (1:3). The concentration of each Ab-modified Ag nanoparticles solution was measured, adjust to 0.14 nM, and the samples were stored at 4° C.

Nanoparticles Characterization:

UV-Vis spectroscopy (Lambda 19, PerkinElmer) and transmission electron microscopy (TEM, JEOL JEM-1011 operating at 100 kV) were used to characterize the optical response, structure, and size of the nanoparticles during the functionalization process. To characterize the codification process, SERS spectra were collected in backscattering geometry with a Renishaw Invia Reflex system equipped with a 2D-CCD detector. The spectrograph used a high resolution grating (1200 g $cm^{-1}$) with additional band pass filter optics. A 785 nm diode laser was focused onto the colloidal solution ([AgO]=0.1 mM) by a long-working distance objective (0.17 NA, working distance 30 mm). The spectra were acquired with an exposure time of 1 s (depending on Raman intensity saturation) and a laser power at the sample of ca. 300 mW.

Bacterial Samples:

Bacteria were inoculated in enriched thioglycollate medium (BBL), incubated at 37° C. for 18 hours and then diluted with saline solution (NaCl 0.9%). Next, the required amount of bacterial solution, to reach the desired final concentration, was added into the corresponding fluid (saline solution or human blood containing Ab-modified Ag nanoparticles (1 µL per mL of sample of each encoded particle) and two-fold of the total amount of codified Ag nanoparticles of unlabeled Ag nanoparticles and protected with serum albumin. To verify the final bacterial concentration per sample, several aliquots of each solution were spread in agar-blood plates and incubated for 24-48 hours at 37° C. After this time, the number of colonies in each plate was counted in order to calculate the CFU $mL^{-1}$. To further corroborate the interaction between the Ab-modified Ag nanoparticles with the corresponding bacteria, equal volumes of Ag nanoparticles (0.14 nM) and bacterial solution (~106 CFU $mL^{-1}$) were mixed, and incubated for 15 min at 37° C. 104 of these mixtures were deposited on carbon coated cupper grids and the samples were allowed to dry before the TEM analysis.

Measurement Setup:

SERS measurements were collected with a Renishaw Invia Reflex. Laser (785 nm, 300 mW) was focused with a macroobjective 6 mm D and 18 mm focal, providing an efficient spot of 0.4 mm. Data collection was set to 270 ms providing and acquisition speed of 1.85 mm $s^{-1}$; providing an evaluation speed of 13.3 min per mL of sample and 3000 scans. Data deconvolution was carried out by applying direct classical least square methods.

Figure 5:
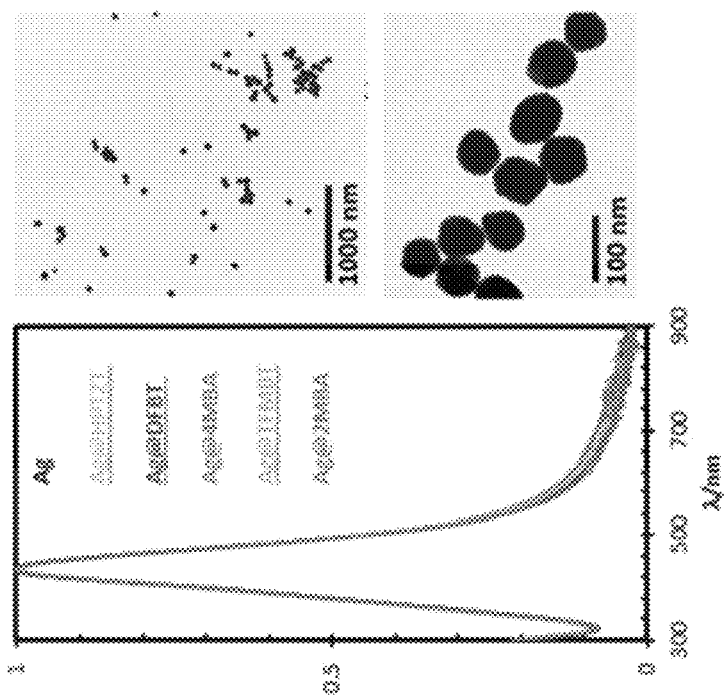
FIG. 5 shows the plasmonic response and representative SEM images of encoded nanoparticles in solution as prepared.

For demonstration of bacteria detection, the inventors prepared five dispersions of coded nanoparticles, each of them functionalized with a different aromatic thiol that yields a unique Raman spectrum (FIGS. 1B and 5). The coded nanoparticles were subsequently and separately functionalized with the corresponding membrane-selective antibody for recognition of, *E. coli* and *P. aeruginosa* (gram negative rod-like bacteria), and *S. aureus* and *S. agalactiae* (gram positive spheroidal coccus). The fifth nanoparticle dispersion was functionalized with serum albumin and used as a blank. All five nanoparticle dispersions were then mixed in the mixing container 101 (FIGS. 1A and 1D) at a concentration of ~107 nanoparticles per mL per Raman code, which we found to be optimum for yielding fast nanoparticle-pathogen attachment with a minimum background SERS signal (see FIG. 6). To limit the formation of spurious aggregates in the colloidal solution, which may lead to false positives, it was added twice as many non-coded BSA-protected nanoparticles to the mixture. Serum contaminated with only one of the four mentioned bacteria was then added to the mixing container 101 of the present invention, and a time series of SERS spectra were collected as the mixture was circulated through the laser focus of the emitter 104 (FIG. 2A and FIGS. 7-10). The majority of the time steps only sampled dispersed nanoparticles, which produced a weak SERS signal. Occasionally, a targeted colony forming unit (CFU) traversed the laser focus, giving rise to ~103 higher SERS signal due to the concentration of particles on the bacterial surface and the subsequent formation of nanoparticle gaps, as we discussed above. Then the correlation of the recorded spectra with the reference ones for each of the Raman codes (FIG. 1B, and calculation details in the SI) is calculated, and obtained clear identification of the added pathogen.

Figure 12:
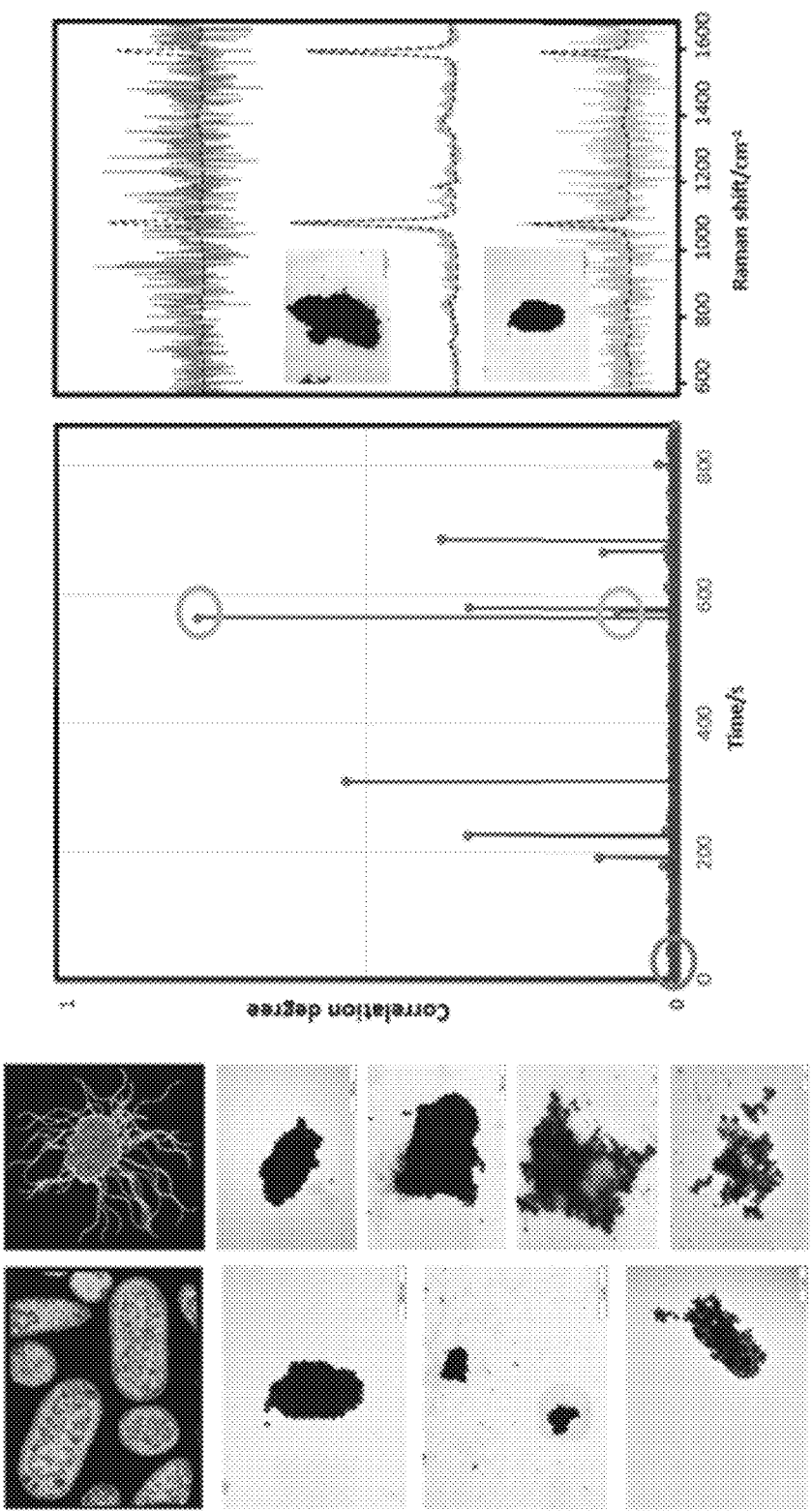
FIG. 12 shows TEM images of several single or clustered *E. coli* (colony forming units, CFU) coated with nanoparticles and revealing the biodiversity of *E. coli*.

The experiment was repeated for samples containing mixtures of two bacteria (FIG. 11). For all the results, it was noted that no false identifications were observed (i.e., no signatures from the bacteria types that were absent from the blood sample), and actually, no positives were recorded from blank samples (FIGS. 2A and 7-12). Incidentally, a significant dispersion in correlation was observed, which it is attributed to the size of the detected CFUs, ranging from single cells to larger colonies (FIG. 12). In all cases, the concentrations obtained were consistent with those found using conventional cell culture but with a considerably lower standard deviation (FIGS. 7-11).

FIG. 12 shows TEM images of several single or clustered *E. coli* cfu as biodiversity of *E. coli* coated with nanoparticles. SERS detection results on the present system for one of the samples of FIG. 8 at low bacterial concentration. Spectra of the highlighted circles showing that the degree of correlation of the SERS spectra of the encoded particle depends on the signal to noise ratio. Thus bigger clusters of bacteria, give rise to better signal and, so, better correlation.

Additionally, it was demonstrated selectivity and multiplexing of the present invention in real blood samples by contaminating blood simultaneously with *S. aureus, E. coli*, and *S. agalactiae* in different concentrations ranging from ~1 to 10's CFUs. The analysis of this sample by the present invention revealed all three pathogens (FIG. 2A and FIG. 13), while a statistical analysis of the results based on three runs of the experiment (FIG. 2C) determined their respective concentrations in excellent agreement with cellular cultures (FIGS. 2B and 13). Incidentally, positive events vary in the degree of correlation (SERS intensity), as expected from the bacterial diversity (FIG. 12). It is stressed that each analysis by the present invention took 13 min, which is a substantial reduction in time compared with cellular cultures (24-72 hours). These results further demonstrate the ability of the present system to classify multiple infected samples with very different pathogen (analyte) concentrations in a single pass and even accurately resolve pathogen (analyte) concentrations in contaminated serum samples with both *E. coli* and a much larger density of *S. aureus* and *S. agalactiae* (FIGS. 2 and 13).

In FIG. 2 the performance of the present invention is shown for blood samples. Particularly in FIG. 2A it is shown the correlation between a temporal series (21-26) of spectra collected over 270 ms intervals and the SERS reference of the labeled nanoparticles (FIG. 1B). The analyzed serum samples contain either one pathogen (21-24, see labels) or no pathogen (25, blank). Series 26 shows the result in a whole blood sample spiked with a combination of three different bacteria and concentrations (*S. aureus, E. coli*, and *S. agalactiae*). Large correlation values reveal the passage of an individual bacteria or CFU. FIG. 2B shows cellular cultures (24-48 hours) for the microorganism inoculated in the blood samples (series 26). White spots correspond to CFUs. FIG. 2C shows the comparison of the corresponding bacteria concentrations as determined by the present invention (open circles) for the sample contaminated with three pathogens (series 26) versus traditional cultures (open squares). Averages over three runs of both the present invention and culture experiments are shown by the corresponding solid symbols.

The kinetics of functionalized nanoparticle aggregation on the pathogen membrane (analyte surface) is a key element of the present invention. As a representative example, after adding a large concentration of *E. coli* to the pool of five coded nanoparticles (time 0), found three distinct stages were found in the temporal evolution of the resulting SERS signal (FIG. 3A): nanoparticle aggregation is initially very slow, as the bacteria are separated from the nanoparticle dispersion, each of them placed in their respective host fluids, so that nanoparticle-bacteria encounters are relatively infrequent, yielding a linear, though slow increase in Raman signal; diffusion eventually brings the nanoparticles closer to the bacteria after ca. 200 s, resulting in more frequent encounters and a faster linear increase in SERS intensity; the signal eventually reaches a plateau after ca. 700 s, indicating saturated coverage of the membrane of the pathogen. The latter stage is also affected by signal depletion produced by flocculation, as the increased weight of nanoparticle-covered CFUs pulls them away from the laser focus. These experimental results can be understood from a Monte Carlo simulation of particle sticking (FIG. 3B), which reveals a characteristic saturation at a nanoparticle random coverage ~60% of the maximum close-packed density[14]. Random occurrence of nanoparticle gaps takes place, leading to an increase in SERS intensity by 3 orders of magnitude compared with non-interacting nanoparticles (cf. solid and broken curves in FIG. 3C), as estimated from the combined effect of attached nanoparticle density and particle gap distance distribution (FIG. 14). The growing in SERS intensity caused by inter-nanoparticles gap hotspot is not linear but exponential (FIG. 3C).

Figure 15:
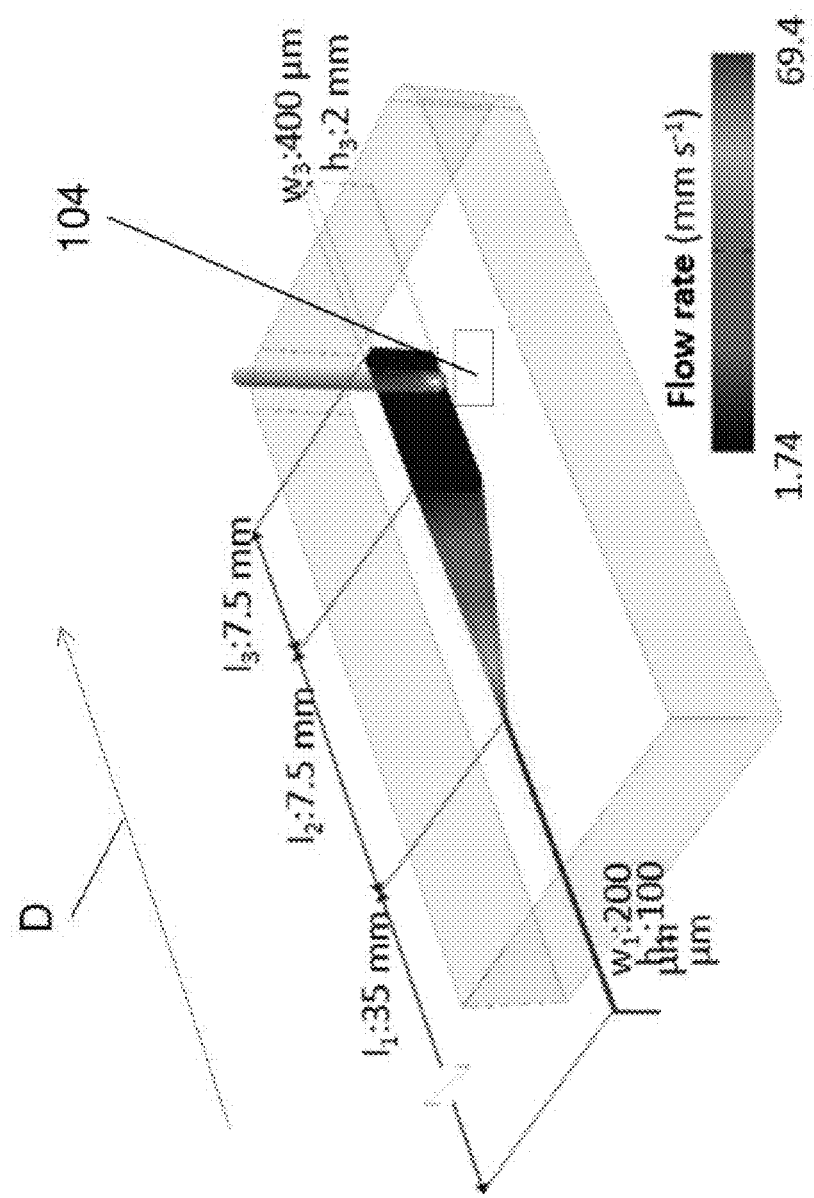
FIG. 15 is a diagrammatical view of sections of a passage of the system according to the invention, wherein dimensions of the sections are schematically and exemplary represented.

Gap formation and the resulting SERS enhancement are thus critical elements that allow obtaining intense signals from bacteria, as an example of analyte, content well above the background of dispersed nanoparticles. A simulation of the near-electric-field light intensity of the 785 nm wavelength laser near a rod-like structure mimicking an *E. coli* specimen (FIG. 3D) shows a mild spatial modulation of the intensity near the microbe accompanied by large enhancement at the nanoparticle gaps. Similar simulations for different particle compositions and sizes (FIG. 15) suggest that gains in sensitivity can be achieved by optimizing these parameters. In particular, the optimum particle size might depend on the dimensions and morphology of the pathogen and its affinity for the nanoparticle ligand biomolecules, as the figure of merit for the present invention is the ratio of the SERS signal coming from the microorganisms to that from the dispersed nanoparticles. Results demonstrate the ability of the present invention to resolve the presence of analytes (bacterial infections, cancer cells, viruses and fungus) much faster than ever before.

Figure 6:
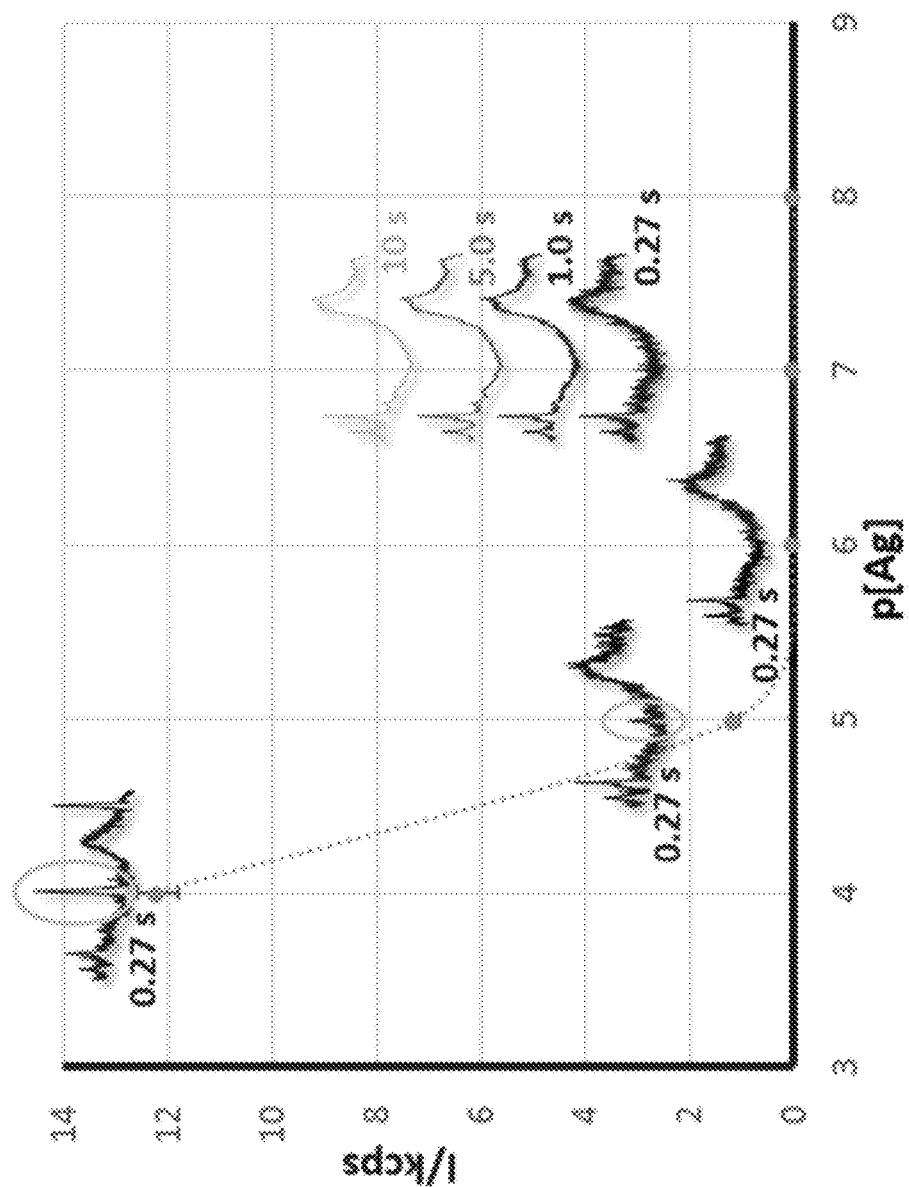
FIG. 6 shows optimization of the concentration of the encoded nanoparticles for the reduction of the background noise into the detection section of the present invention. Although a SERS signal can be clearly identified above $10^{-5}$ M in silver, at $10^{-6}$ M the spectrum disappears. At $10^{-7}$ M (working concentration) no signal is achieved from the dispersed nanoparticles background even when largely increasing the acquisition time.
Figures 7A, 7B, 7C:
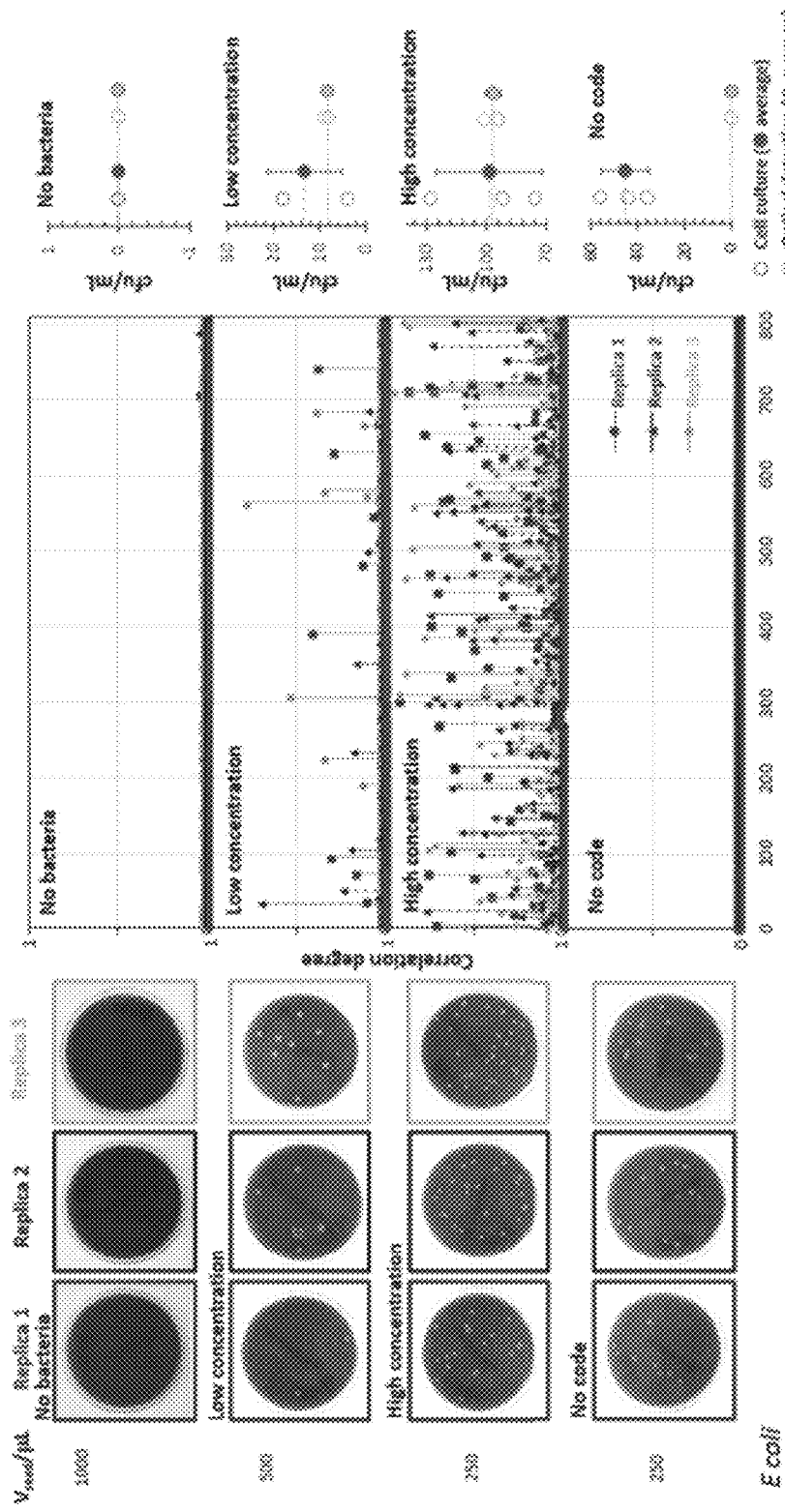
FIG. 7A shows images of cellular cultures for an analyte (*E. coli* bacteria); a serum sample is spiked with *E. coli* at different concentrations.
FIG. 7B shows the detection and quantification results obtained in the present system: with either with no bacteria present, with low concentration, with high concentration or with high concentration but without the encoded nanoparticle that identifies the analyte (*E. coli* bacteria)
FIG. 7C shows a statistical comparison of methods of FIGS. 7A and 7B.
Figure 8A:
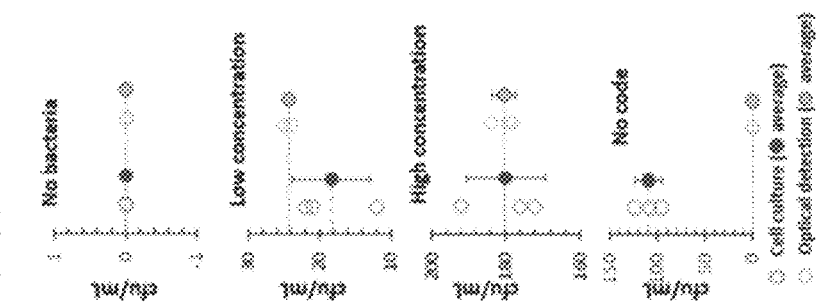
FIG. 8A shows images of cellular cultures for an analyte (*S. aureus* bacteria); a serum sample is spiked with *S. aureus* at different concentrations.
Figure 8B:
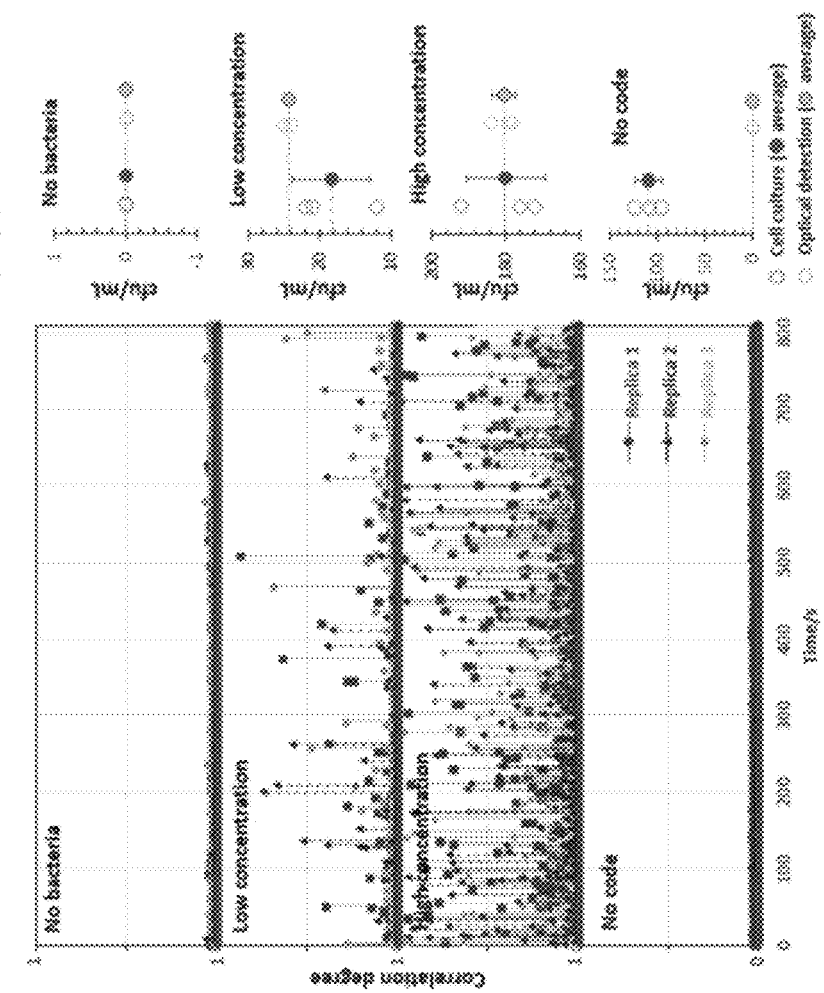
FIG. 8B shows the detection and quantification results obtained in the present system: with no bacteria present, at low concentration, high concentration and high concentration but without the encoded nanoparticle that identifies the analyte (*S. aureus* bacteria)
Figure 8C:
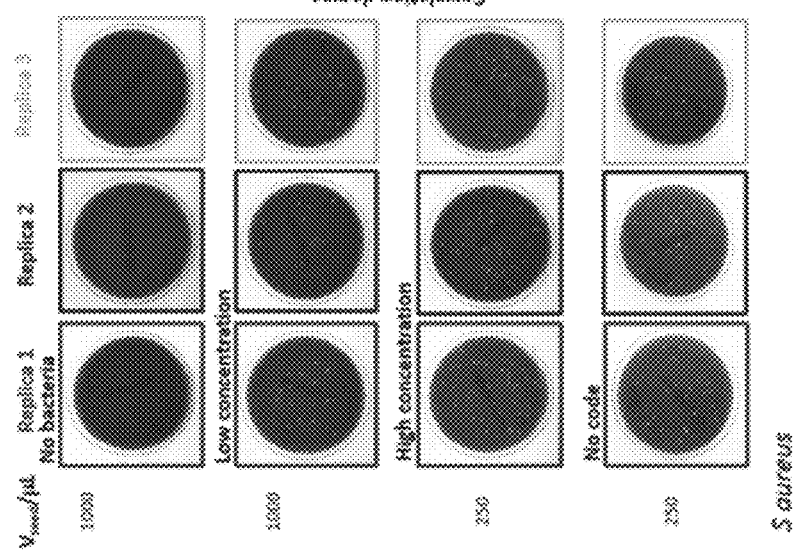
FIG. 8C shows a statistical comparison of methods of FIGS. 8A and 8B.
Figures 9A, 9B, 9C:
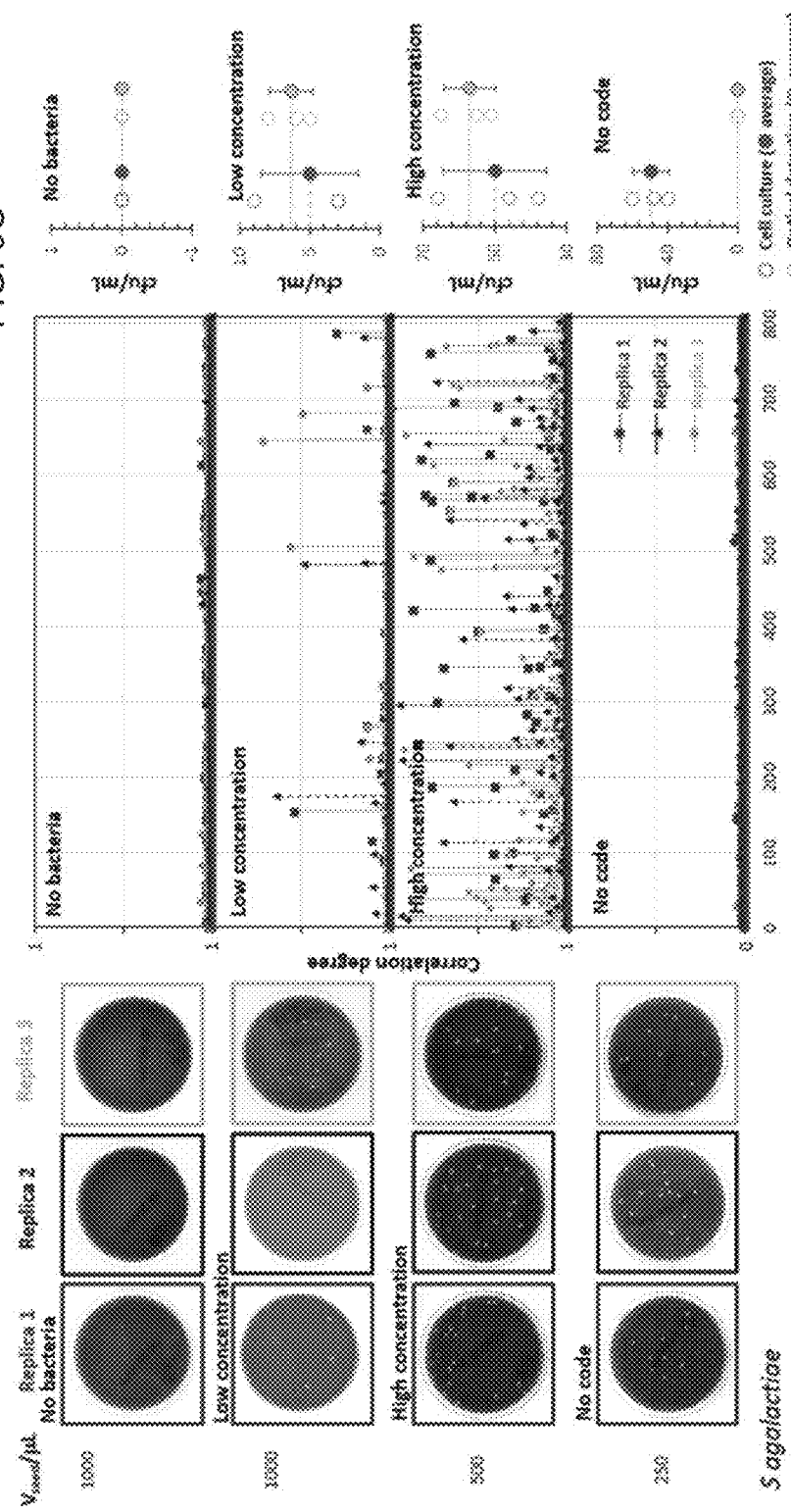
FIG. 9A shows images of cellular cultures for an analyte (*S. agalactiae* bacteria); a serum sample is spiked with *S. agalactiae* at different concentrations.
FIG. 9B shows the detection and quantification results obtained in the present system: with no bacteria present, at low concentration, high concentration and high concentration but without the encoded nanoparticle that identifies the analyte (*S. agalactiae* bacteria)
FIG. 9C shows a statistical comparison of methods of FIGS. 9A and 9B.
Figure 14B:
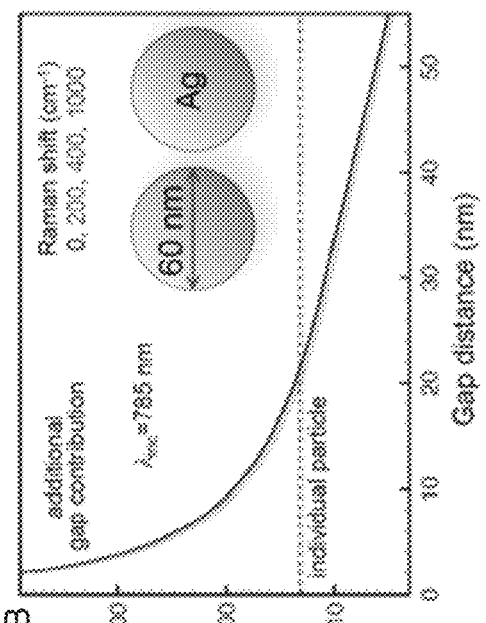
FIG. 14B shows SERS enhancement in Ag nanoparticle dimers, from an electromagnetic simulation.
Figure 14D:
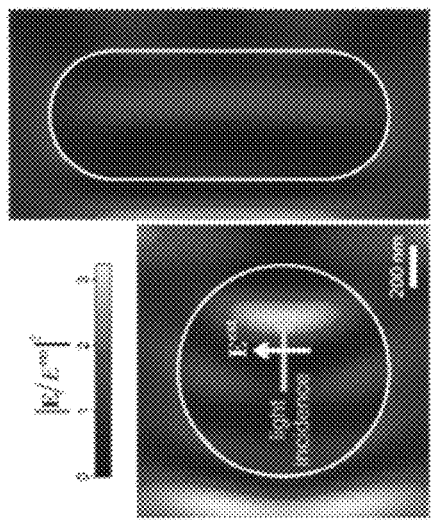
FIG. 14D shows effective response of a particle layer.
Figure 14A:
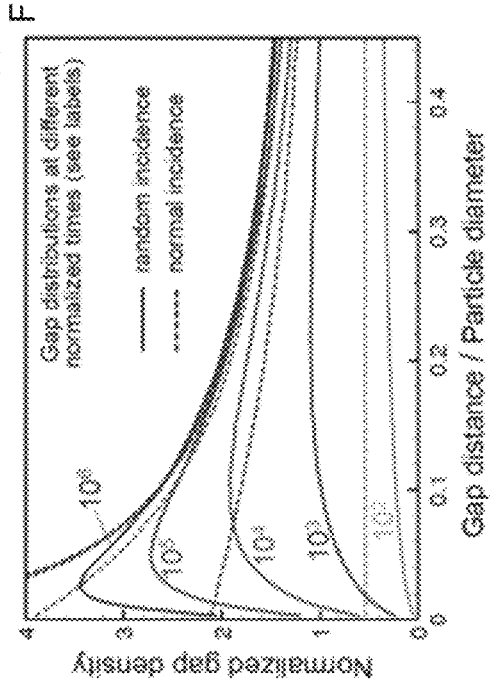
FIG. 14A shows the distribution of gap distances, as extracted from the Monte Carlo simulation of FIG. 3B.
Figure 14C:
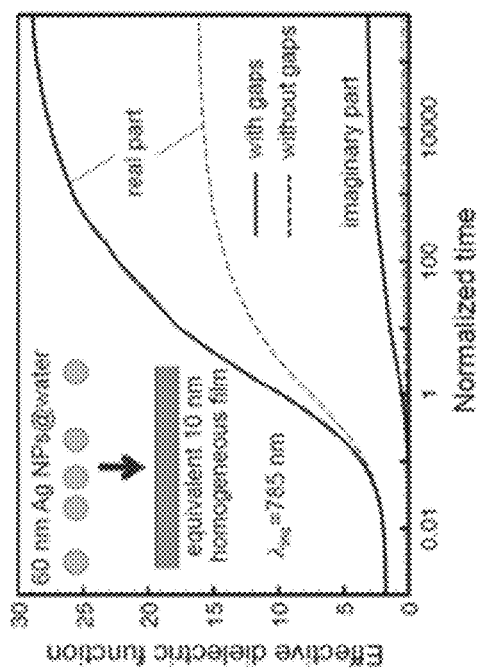
FIG. 14C shows temporal evolution of the SERS signal, as extracted from the data of FIGS. 14A and 14B.

It should be noted further to the present invention that FIG. 14A shows the distribution of inter-particle gap distances at different normalized time steps (see labels) based upon the Monte Carlo simulations of FIG. 6, both under random (solid curves) or normal (dashed curves) incidence directions. The gap density distribution is normalized to the maximum possible nanoparticle density and it is given per unit of gap-to-diameter ratio. FIG. 14B shows SERS enhancement in Ag nanoparticle dimers. It particularly shows increase in SERS enhancement factor due to inter-particle interaction (solid curves) relative to the values for individual particles (dashed lines) as a function of gap distance. The enhancement factor is calculated by solving Maxwell's equations at the frequency of both the incident light and the inelastically scattered Raman signal. The boundary-element method is used to solve these equations [21]. The aqueous solution is modelled through a medium of permittivity equal to 1.77. The silver medium is modelled through its tabulated complex permittivity[22]. The product of the near-field intensity enhancements at both frequencies gives an estimate of the Raman enhancement. Each of the field enhancements is averaged over light polarization and random directions of incidence relative to the dimer orientation. The estimated SERS enhancement is averaged over randomly distributed molecules placed 1 nm outside the Ag surface. The different Raman shifts under consideration produce similar results because the incident light wavelength (785 nm) is not resonant with the particle plasmons (see FIG. 5). FIG. 14C shows temporal evolution of the SERS signal. The gap-mediated SERS enhancement (FIG. 5) and the time-dependent particle (FIG. 6) and gap (FIG. 7) densities are combined to produce the evolution of the SERS signal. The vertical axis gives the intensity integrated over 1 $\mu m^2$ of planar surface, normalized to that of an individual nanoparticle. The time is normalized as in FIG. 5. The solid (dashed) curve shows results with (without) inclusion of gap enhancement effects. Random incidence assumed for the nanoparticles (see FIGS. 6 and 7)

Regarding FIG. 14D, the effective dielectric function of a thin homogeneous film that has the same normal-incidence reflection coefficient as the randomly distributed particle layer was calculated. The latter is estimated from the dipoles induced per gap and per particle, as obtained from electromagnetic simulations of the gap-size-dependent polarizability of nanoparticle dimers (not shown). The effective dielectric function is then obtained as $\varepsilon_0+(4\pi/t)P$, where P is surface density of induced dipoles, t=10 nm is the equivalent film thickness, and $\varepsilon_0=1.77$ is the permittivity of the surrounding medium. It should be pointed out that the near field produced by this type of material is rather insensitive to the actual choice of t (e.g., a choice of t=20 nm renders nearly undistinguishable results from those of FIG. 14D).

Therefore the inventors demonstrate exhaustive analyte (pathogen) identification through fast screening of large body-fluid volumes (for instance milliliters of blood) for analyte (bacterial) content, as required for instance by standard medical practice for the analysis of biological samples [13]. Specifically, label-free detection and quantification of analyte (bacteria) in real time and in a multiplexed manner.

Figure 4:
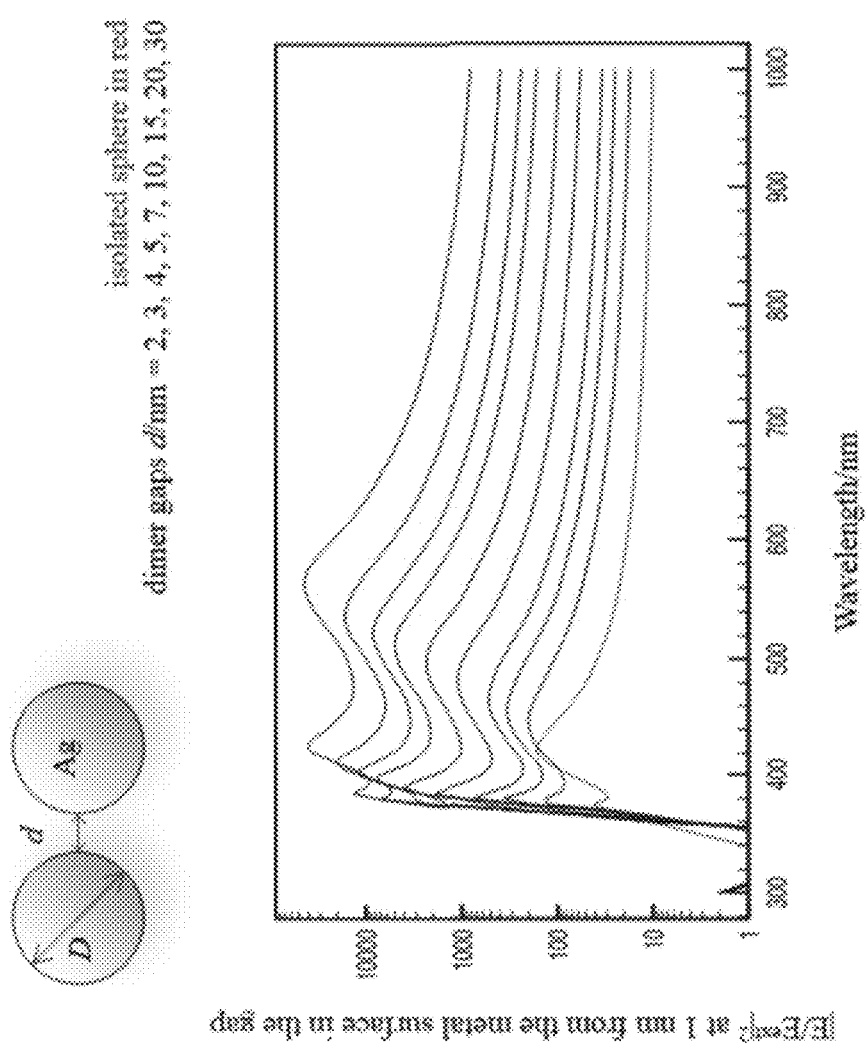
FIG. 4 shows the electric field generated at the centre of the gap separating two silver colloidal nanoparticles of 60 nm of diameter as a function their distance interaction when forming a dimer.

Furthermore, it was demonstrated that the nanoparticles produce a relatively weak Raman signal when they are dispersed in a fluid. In contrast, the presence of one of the targeted analytes (pathogens) triggers the accumulation of its partner nanoparticles on the analyte (antigen-carrying membrane of the microorganism), rapidly reaching full random coverage[14]. Multiple gaps between nanoparticles are then formed, which act as optical hotspots in which Raman scattering is enhanced by several orders of magnitude (for instance between 2 and 3 orders) relative to non-interacting nanoparticles (FIGS. 1A and 4)[15]. The resulting surface-enhanced Raman scattering (SERS) signal is sufficiently intense as to allow recording a pathogen-specific inelastic light spectrum (FIG. 1B) for the nanoparticle-covered bacteria (FIG. 10). That intense signal is received (by reader 105) and processed (by control means 106) comparing it to weak signals of non-interacting nanoparticles. By driving the sample through the passage 102A, 102B, 102C preferably with different dimension as above describe, where a backscattered detecting laser (785 nm) continuously monitors the liquid stream (one spectrum every 270 ms over an illuminated volume of ~0.3 µL), four different types of bacteria were successfully screened and simultaneously quantified at a pace of 13 minutes per mL of blood. Importantly, this method can be readily scaled to cope with many more analytes (pathogens including virus or eukaryotic cells such as fungi or protozoa, cancer cells, etc.), in a single pass without an increase in sampling time, simply by preparing nanoparticles functionalized with more combinations of Raman labels and specific ligands.

The details, shapes, sizes and other accessorial elements, likewise the materials used in the manufacture of the method for detection of analytes in fluids and the optical detection system for carrying out such method of the invention can be appropriately substituted by others that are technically equivalent and do not depart from the scope defined by the claims that are included below.

REFERENCES

[1] D. C. Angus, T. van der Poll, Severe Sepsis and Septic Shock. New England Journal of Medicine 369, 840 (2013).

[2] A. Kumar et al., Duration of hypotension before initiation of effective antimicrobial therapy is the critical determinant of survival in human septic shock. Critical care medicine 34, 1589 (June 2006).

[3] P.-E. Fournier et al., Modern clinical microbiology: new challenges and solutions. Nat Rev Micro 11, 574 (August//print, 2013).

[4] R. M. T. De Wildt, C. R. Mundy, B. D. Gorick, I. M. Tomlinson, Antibody arrays for high-throughput screening of antibody-antigen interactions. Nature Biotechnology 18, 989 (2000).

[5] R. P. H. Peters, M. A. V. Agtmael, S. A. Danner, P. H. M. Savelkoul, C. M. J. E. Vandenbroucke-Grauls, New developments in the diagnosis of bloodstream infections. Lancet Infectious Diseases 4, 751 (2004).

[6] T. Maier, S. Klepel, U. Renner, M. Kostrzewa, Fast and reliable MALDI-TOF MS-based microorganism identification. Nature Methods 3, i (2006).

[7] M. Perros, A sustainable model for antibiotics. Science 347, 1062 (Mar. 6, 2015).

[8] R. Kanthor, Diagnostics: Detection drives defence. Nature 509, S14 (May 1, 2014/print).

[9] D.-K. Kang et al., Rapid detection of single bacteria in unprocessed blood using Integrated Comprehensive Droplet Digital Detection. Nat Commun 5, (Nov. 13, 2014/online).

[10] W. Chen et al., Identification of Bacteria in Water by a Fluorescent Array. Angewandte Chemie International Edition 53, 13734 (2014).

[11] Y. Wang, B. Yan, L. Chen, SERS Tags: Novel Optical Nanoprobes for Bioanalysis. Chemical Reviews 113, 1391 (Mar. 13, 2013).

[12] H.-Y. Lin et al., On-line SERS Detection of Single Bacterium Using Novel SERS Nanoprobes and A Microfluidic Dielectrophoresis Device. Small 10, 4700 (2014).

[13] F. R. Cockerill et al., Optimal Testing Parameters for Blood Cultures. Clinical Infectious Diseases 38, 1724 (Jun. 15, 2004).

[14] J. W. Evans, Random and cooperative sequential adsorption. Reviews of Modern Physics 65, 1281 (Oct. 1, 1993).

[15] F. J. Garcia de Abajo, Optical excitations in electron microscopy. Reviews of Modern Physics 82, 209 (Feb. 3, 2010).

[16] P. C. Lee, D. Meisel, Adsorption and surface-enhanced Raman of dyes on silver and gold sols. The Journal of Physical Chemistry 86, 3391 (Aug. 1, 1982).

[17] H. Li et al., Synthesis of Monodisperse, Quasi-Spherical Silver Nanoparticles with Sizes Defined by the Nature of Silver Precursors. Langmuir 30, 2498 (Mar. 11, 2014).

[18] H. Li, H. Xia, D. Wang, X. Tao, Simple Synthesis of Monodisperse, Quasi-spherical, Citrate-Stabilized Silver Nanocrystals in Water. Langmuir 29, 5074 (Apr. 12, 2013).

[19] B. Mir-Simon, I. Reche-Perez, L. Guerrini, N. Pazos-Perez, R. A. Alvarez-Puebla, Universal One-Pot and Scalable Synthesis of SERS Encoded Nanoparticles. Chemistry of Materials 27, 950 (Feb. 10, 2015).

[20] D. Paramelle et al., A rapid method to estimate the concentration of citrate capped silver nanoparticles from UV-visible light spectra. Analyst 139, 4855 (2014).

[21] F. J. Garcia de Abajo and A. Howie, Retarded field calculation of electron energy loss in inhomogeneous dielectrics, Phys. Rev. B 65, 115418 (2002).

[22] P. B. Johnson and R. W. Christy, Optical constants of the noble metals, Phys. Rev. B 6, 4370-4379 (1972).

What is claimed is:

1. A method for detection of presence or absence of analytes in fluids, comprising the steps of:
   a) contacting a fluid sample and a plurality of silver nanoparticles, wherein each of the plurality of silver nanoparticles comprises, a core unprotected and tagged with at least a molecular species with a defined surface-enhanced Raman scattering (SERS) spectrum, the nanoparticles being functionalized with at least a selective ligand for a given receptor of a target analyte, the contact of the fluid sample with the nanoparticles being under conditions such that, when the fluid sample comprises at least an analyte, the nanoparticles aggregate selectively on a surface of theft target analyte forming a nanoparticle-analyte complex, the aggregation promoting the concentration of the nanoparticles on the surface of the target analyte and thus a plasmon coupling in between the nanoparticles through the generation of at least one narrow inter-nanoparticle gap;
   b) circulating a fluid mixture of the fluid sample and the plurality of nanoparticles through at least a passage;
   c) subjecting the fluid mixture of the fluid sample and the plurality of nanoparticles to SERS;
   d) measuring at least a SERS signal associated with the fluid mixture;
   e) spectrally analysing the at least one SERS signal of step d);
   f) recognizing at least one defined SERS spectrum of the nanoparticle-analyte complex, through a SERS signal enhanced by the at least one narrow inter-nanoparticle gap, when the fluid mixture comprises at least a nanoparticle-analyte complex with the narrow inter-nanoparticle gap; and
   g) quantifying the number of recognized SERS spectra and the intensity of the SERS signal related to each recognized defined SERS spectra in the fluid mixture.

2. A method for detection of presence or absence of analytes in fluids according to claim 1, wherein in step e) a SERS spectrum is recorded in predefined lapses of time.

3. A method for detection of presence or absence of analytes in fluids according to claim 1, wherein the analyte is one of: eukaryotic and prokaryotic cells, including circulating tumoral cells, pathogenic and no pathogenic microorganism as fungi, protozoa, algae, rotifers, bacteria and archaea, viruses, nucleic acids, peptide nucleic acids, antigens, peptides and proteins or the combination thereof.

4. A method for detection of presence or absence of analytes in fluids according to claim 1, wherein the selective ligand is an antibody, protein, aptamer or small molecule.

5. A method for detection of presence or absence of analytes in fluids according to claim 1, wherein the selective ligand is a cancer cell marker.

6. The method of claim 1, further comprising tagging the nanoparticles with the at least a molecular species using a bond having covalent character.

7. The method of claim 1, further comprising enhancing the SERS signal with the at least one narrow inter-nanoparticle gap by 3 orders of magnitude compared to a signal associated with nanoparticles that are not aggregated into a nanoparticle-analyte complex.

* * * * *